USD07053236B2

(12) United States Patent
Deng et al.

(10) Patent No.: US 7,053,236 B2
(45) Date of Patent: *May 30, 2006

(54) CATALYTIC ASYMMETRIC DESYMMETRIZATION OF PROCHIRAL AND MESO COMPOUNDS

(75) Inventors: Li Deng, Waltham, MA (US); Yonggang Chen, Somerville, MA (US); Shikai Tian, Waltham, MA (US)

(73) Assignee: Brandeis University, Waltham, MA (US)

( * ) Notice: Subject to any disclaimer, the term of this patent is extended or adjusted under 35 U.S.C. 154(b) by 259 days.

This patent is subject to a terminal disclaimer.

(21) Appl. No.: 10/460,051

(22) Filed: Jun. 12, 2003

(65) Prior Publication Data

US 2004/0082809 A1    Apr. 29, 2004

Related U.S. Application Data

(63) Continuation-in-part of application No. 10/366,581, filed on Feb. 13, 2003, which is a continuation of application No. 09/825,167, filed on Apr. 3, 2001, now Pat. No. 6,580,003.

(60) Provisional application No. 60/194,520, filed on Apr. 4, 2000.

(51) Int. Cl.
    *C07C 67/00*    (2006.01)
(52) U.S. Cl. ............... 560/127; 560/192; 560/204; 560/127; 562/590; 544/351
(58) Field of Classification Search ............... 544/351; 562/590; 560/127, 192, 204
See application file for complete search history.

(56) References Cited

U.S. PATENT DOCUMENTS 2,566,957 A    9/1951    Pedlow et al. ............... 428/420

FOREIGN PATENT DOCUMENTS

GB    1045091    10/1966

OTHER PUBLICATIONS

Hawley, Gessner, "the Condensed Chemical Dictionary", 1977, Van Nostrand, New York, p. 626.
Kolasa, T. et al., "Syntheses of Functionalized β-Lactams from Tartaric Acid", *Tetrahedron*, 45(10:3071-3080 (1989).
John D. Roberts and Marjorie C. Caserio, "Basic Principles of Organic Chemistry", Benjamin, New York, 1964, pp. 288, 289.
Aitken et al.; "Catalytic asymmetric Synthesis of Highly Functionalised Compounds With Six Contiguous Stereocentre", J. Chem. Soc. Chem. Commun, pp. 632-634, (1988).
Aitken et al.; "Catalytic Asymmetric Synthesis of Highly Functionalised Compounds with Six Contiguous Stereocentres", J. Chem. Soc. Chem. Commun. pp. 632-634, (1988).

(Continued)

*Primary Examiner*—James O. Wilson
*Assistant Examiner*—Paul V. Ward
(74) *Attorney, Agent, or Firm*—Dana M. Gordon; Foley Hoag LLP

(57) ABSTRACT

The present invention relates to methods for the synthesis of chiral non-racemic products, e.g., enantiomerically-enriched hemiesters, from prochiral and meso starting materials, e.g., prochiral and meso cyclic anhydrides. The present invention also relates to catalysts for the aforementioned methods, and methods for synthesizing these catalysts.

28 Claims, 17 Drawing Sheets

| Entry | Catalyst | Solvent | ee (%) of Product |
|---|---|---|---|
| 1 | Quinidine | Toluene | 64 |
| 2 | (DHQD)₂PYR | Toluene | 13 |
| 3 | (DHQD)₂PHAL | Toluene | 18 |
| 4 | (DHQD)₂AQN | Toluene | 85 |
| 5 | DHQD-PHN | Toluene | 81 |
| 6 | DHQD-CLB | Toluene | 32 |
| 7 | DHQD-MEQ | Toluene | 31 |
| 8 | (DHQD)₂AQN | CCl₄ | 88 |
| 9 | (DHQD)₂AQN | Et₂O | 93 |
| 10 | (DHQD)₂AQN | CHCl₃ | 82 |
| 11 | (DHQD)₂AQN | Hexane | 54 |
| 12 | (DHQD)₂AQN | THF | 89 |
| 13 | (DHQD)₂AQN | ᵗBuOMe | 92 |
| 14 | (DHQD)₂AQN | MeCN | 71 |
| 15 | (DHQD)₂AQN | CH₂Cl₂ | 73 |

OTHER PUBLICATIONS

Aitken and Gopal, "Catalytic Asymmetric Ring-openning of Bridged Tricyclic Anhydrides", Tetrahedron Asymmetry 1(8): 517-520, (1990).

Albers et al.; "Desymmetrisation of meso-Anhydrides Utilising (S)-Proline Derivatives", Synthesis, pp. 393-398, (Mar. 1996).

Aldrich Chemical Company, p. 1165, Item # 13,689-1, (1992).

Berkowitz et al.; "Enzyme-Assisted Asymmetric total Synthesis of (−)-Podophyllotoxin and (−)- Picropodophyllin", J. Org. Chem. 65: 847-860, (2000).

Borzilleri and Weinreb; "Total Synthesis of Popuamine via a Stereospecific Intramolecular Imino Ene Reaction of an Allenylsilane", J. Am. Chem. Soc., 116:9789-9790, (1994).

Borzilleri et al; "Total Synthesis of the Unusual Marine Alkaloid (−)- Papuamine Utilizing a Novel Imino Ene Reaction", J. Am. Chem. Soc. 117: 10905-10913, (1995).

Brion et al; "Stereoselective synthesis of a Trans-Octahydroindole Drivative. Precursor of Trandolapril (RU 44 570), an Inhibitor of Angiotensin Converting Enzyme", Tetrahedron Letters 33(34): 4889-4892. (1992).

Becker and Sharpless; "A New Ligand Class for the Asymmetric Dihydroxylation of Olefin", Angew Chem. Int. Ed. Engl., 35(4):448-450, (1996).

Bolm et al.; "Simple and Highly Enantioselective Noenzymatic Ring Opening of Cyclic Prochiral Anhydrides", Synlett, No. 2 : 195-196. (1999).

Couché et al.; "The Synthesis of Highly Functionalized Enantiometrically Enriched Cyclohexanes. An Approach to Carba-Sugars and Aminocarba-Sugars." Synlett, No. 1:87-89, (1999).

Evans et al; "$C_2$-Symmetric Cu(I I) Complexes as Chiral Lewis Acids. Catalytic Enantioselective Michael Addition of silylketene Acetals to Alkylidene Malonates", J. Am. Chem. Soc. 121: 1994-1995, (1999).

Grant and Grant, "Grant & Hackh's Chemical Dictionary", $5^{th}$ Edition, Mcgraw-Hill, New York, pp. 558-559, (1990).

Hawley, Gessner, "the Condensed Chemical Dictionary", Van Nostrand, New York, pp. 823, (1997).

Heathcock et al.; "Total Synthesis and Biological Evaluation of Structural analogues of Compactin and Dihydromevinolin", J. Med. Chem. 30: 1858-1873, (1987).

Hecker and Heathcock,; "Total Synthesis of (+)-Dihydromevinolin", J. Am. Chem. Soc. 108: 4586-4594, (1986).

Hiratake et al.; "Catalytic Asymmetric Induction from ProchiralnCyclic Acid Anhydrides Using Cinchona Alkaloids", J. Chem. Soc., Chem. Commun. pp. 1717-1719, (1985).

Hiratake et al.; "Enantiotopic-Group Differentiation. Catalytic Asymmetric Ring-Opening of Prochiral Cyclic Acid Anhydrides with Methanol, Using Cinchona Alkaloids", J. chem. Soc. Perkin Trans. 1: 1053-1058, (1987).

Jaeschke and Seebach,; "Highly Enantioselective Ring Opening of Cyclic Meso-Anhydrides to Isopropyl Hemiesters with Ti-TADDOlates: an alternative to Hydrolytic Enzymes?", J. Org. Chem. 63: 1190-1197, (1998).

John and Caserio, "Basic Principlesof Organic Chemistry", Benjamin, New York, p. 288 & 289, (1964).

Kolasa and Miller; "Synthesis of Functionalized β-Lactnams From Tartaric Acid", Tetrahedron, 45(10): 3071-3080, (1989).

Konoike and Araki, "Practical Synthesis of Chiral Synthons for the Preparation of HMG-CoA Reductase Inhibitors", J. Org. Chem. 59: 7849-7854( 1994).

Ohtani et al.; "Enantioselective Synthesis of S-1452, an Orally Active Potent Thromboxane $A_2$ Receptor Antagonist", J. Org. Chem. 56: 2122-2127, (1991).

Ohtani et al.; "Highly Effective and Practical Enantioselective Synthesis of Half-Esters of Bicyclo[2.2.1]heptanedicarboxylic Acid", J. Org. Chem. 56: 4120-4123 (1991).

Ozegowski et al. "The Different Behaviour of Syn-and Anti-2,3 Dimethylbutanedioic Anhydride in the Lipase-Catalyzed Enantioselective Alcoholysis" Tetrahedron Asymmetry 6(5): 1191-1194, (1995).

Paterson et al; "Studies in Marine Macrolide Synthesis: Stereocontrolled Synthesis of the $C_1$-$C_{11}$ and $C_{15}$—$C_{27}$ Subunits of Aplyronine A", Tetrahedron Letters 39: 6037-6040, (1998).

Rosen and Heathcock,; "Total Synthesis of (+)- Compactin", J. Am. Chem. 107:3731-3733, (1985).

Seebach et al.; "Highly Enantioselective Opening of Cyclic meso-Anhydrides to Isopropyl Hemiesters With Diisopropoxytitanium TADDOLates", Angew. Chem. Int. Ed. Engl. 34(21): 2395-2396, (1995).

Shimizu et al.; "Enantioselective Esterification of Cyclic Discarboxylic Anhydrides Using Chiral Aminol Alcohols as Auxiliaries", Bull. Chem. Soc. Jpn 66(7): 2128-2130, (1993).

Suzuki et al; "A Simple Synthesis of Bicyclo [2.2.1] Heptane System, A Key Potential Intermediate for Stable Prostaglandin $H_2$ Analogue", Heterocycles 14(11): 1735-1738, (1980).

Theisen et al.; "Prochiral Recognition in the Reaction of 3-Substituted Glutaric Anhydrides with Chiral Secondary Alcohols", J. Org. Chem. 58: 142-146, (1993).

Toyota et al; "First total Synthesis of (±)-Methyl Gummiferolate Using a Homoallyl- Homoallyl Radical Rearrangement Reaction", 1(10): 1627-1629, (1999).

Wender et al.; "Synthetic Studies on Arene-Olefin Cycloadditions. 11. Total Synthesis of (−)-Retigeranic Acid", Tetrahedron Letters 31(18): 2517-2520, (1990).

Yamamoto et al.; Asymmetric Ring Opening of Cyclic Acid Anhydridess With Lipase in Organic Solvents, Tetrahedron Letters, pp. 1717-1720, (1988).

Yamamoto et al. "Asymmetric Synthesis of Optically Active Lactones from Cyclic Acid Anhydrides Using Lipase in Organic Solvents", Agric. Biol. Chem. 52(12): 3087-3092, (1988).

| Entry | Catalyst | Solvent | ee (%) of Product |
| --- | --- | --- | --- |
| 1 | Quinidine | Toluene | 64 |
| 2 | (DHQD)$_2$PYR | Toluene | 13 |
| 3 | (DHQD)$_2$PHAL | Toluene | 18 |
| 4 | (DHQD)$_2$AQN | Toluene | 85 |
| 5 | DHQD-PHN | Toluene | 81 |
| 6 | DHQD-CLB | Toluene | 32 |
| 7 | DHQD-MEQ | Toluene | 31 |
| 8 | (DHQD)$_2$AQN | CCl$_4$ | 88 |
| 9 | (DHQD)$_2$AQN | Et$_2$O | 93 |
| 10 | (DHQD)$_2$AQN | CHCl$_3$ | 82 |
| 11 | (DHQD)$_2$AQN | Hexane | 54 |
| 12 | (DHQD)$_2$AQN | THF | 89 |
| 13 | (DHQD)$_2$AQN | $^t$BuOMe | 92 |
| 14 | (DHQD)$_2$AQN | MeCN | 71 |
| 15 | (DHQD)$_2$AQN | CH$_2$Cl$_2$ | 73 | prochiral or *meso* cyclic anhydride  →  (DHQD)₂AQN, MeOH  →  chiral non-racemic product 60-95% yield

| Entry | Anhydride | Catalyst Loading (mole %) | Solvent | Temp. (°C) | ee (%)[c] | Product[b] |
|---|---|---|---|---|---|---|
| 1 |  | 5 | Ether | -20 | 98 (98) | CO₂H, CO₂Me |
| 2 | | 30 | Ether | -35 | 91 (82) | CO₂H, CO₂Me |
| 3 | | 30 | Ether | -35 | 90 (83) | b, CO₂H, CO₂Me |
| 4 | | 10 | Toluene | r.t. | 76[a] | CO₂H, CO₂Me |

60-95% yield

| Entry | Anhydride | Catalyst Loading (mole %) | Solvent | Temp. (°C) | ee (%)[c] | Product[b] |
|---|---|---|---|---|---|---|
| 5 | | 10 | Ether | -30 | 96 | |
| 6 | | 5 | Ether | -20 | 97 | |
| 7 | | 7 | Ether | -20 | 98 | [b] |
| 8 | | 10 | Ether | -30 | 98 | [b] |

60-95% yield

| Entry | Anhydride | Catalyst Loading (mole %) | Solvent | Temp. (°C) | ee (%)[c] | Product[b] |
|---|---|---|---|---|---|---|
| 9 | (norbornane-fused anhydride) | 15 | Ether | -30 | 90 | (norbornane with CO₂Me, CO₂H) [b] |
| 10 | (oxanorbornene-fused anhydride) | 20 | Ether | -20 | 95 | (oxanorbornene with CO₂H, CO₂Me) |
| 11 | (oxanorbornane-fused anhydride) | 15 | Ether | -20 | 92 | (oxanorbornane with CO₂H, CO₂Me) [b] |

(DHQ)₂PHAL (DHQD)₂PHAL (DHQ)₂PYR (DHQD)₂PYR (DHQ)₂AQN (DHQD)₂AQN

DHQ-CLB

DHQD-CLB

DHQ-MEQ

DHQD-MEQ

DHQ-AQN

DHQD-AQN

DHQ-PHN

DHQD-PHN

QD-PP

QD-TB

Q-PP

Q-TB

| Entry | ROH | Catalyst Loading (mole %) | Solvent | Temp. (°C) | ee (%) | Product |
|---|---|---|---|---|---|---|
| 1 | MeOH | 5 | Ether | r.t. | 93 | ![](CO2H/CO2Me) |
| 2 | EtOH | 5 | Ether | r.t. | 95 | ![](CO2H/CO2Et) |
| 3 | EtOH | 10 | Ether | r.t. | 97 | ![](CO2H/CO2Et) |
| 4 | iPrOH | 10 | Ether | r.t. | | No Reaction | meso cyclic anhydride —(DHQD-PHN, MeOH)→ chiral non-racemic product

| Entry | Anhydride | Catalyst Loading (mole %) | Solvent | Temp. (°C) | ee (%)[a] | Product[b] |
|---|---|---|---|---|---|---|
| 1 |  | 5<br>15<br>30 | Toluene<br>Toluene<br>Toluene | r.t.<br>-30<br>-30 | 81<br>95<br>96 |  |
| 2 |  | 10 | Toluene | r.t. | 19 |  |
| 3 |  | 5 | Ether | r.t. | 88 |  [b] |
| 4 |  | 3 | CCl₄ | r.t. | 78 |  [b] |

| Substrate | Catalyst | Alcohol | Reaction Time (h) | Conversion % (% Yield) | Ee (%) |
|---|---|---|---|---|---|
|  | QD-PP | MeOH | 77.5 | 92% (69%) | 77% |
|  | QD-PP | CF$_3$CH$_2$OH | 70.5 | 93% (65%) | 77% |
|  | QD-PP | MeOH | 52 | 91.5% (73%) | 79% |
|  | QD-PP | CF$_3$CH$_2$OH | 71.5 | 97% (89%) | 81% |
|  | QD-PP | MeOH | 91 | 90.3% (72%) | 80% |
|  | QD-PP | CF$_3$CH$_2$OH | 91 | 90.9% (70%) | 55% |
|  | QD-PP | MeOH | 105 | 91.5% (45.7%) | 78% |
|  | QD-PP | CF$_3$CH$_2$OH | 105 | 87.4% (68.3%) | 48% |

| Substrate | Catalyst | Catalyst (mol%) | Alcohol | Alcohol (equiv) | Temp. (C) | Reaction Time (h) | Conversion % (% yield) | Ee (%) |
|---|---|---|---|---|---|---|---|---|
|  | QD-PP | 20 | CF₃CH₂OH | 10 | RT | 2 | 100 (99) | 90 |
|  | QD-PP | 20 | CF₃CH₂OH | 10 | -27 | 48 | 100 (92) | 94 |
|  | QD-PP | 20 | CF₃CH₂OH | 10 | RT | 5 | 100 (75) | 89 |
|  | QD-PP | 20 | CF₃CH₂OH | 10 | -27 | 16 | 100 (87) | 91 |
|  | QD-PP | 20 | CH₃OH | 10 | -27 | 192 | 65 (93) | 96 |

| Substrate | Catalyst | Catalyst (mol%) | Alcohol | Alcohol (equiv) | Temp. (C) | Reaction Time (h) | Conversion % (% yield) | Ee (%) |
|---|---|---|---|---|---|---|---|---|
|  | QD-PP | 30 | CH₃OH | 10 | -27 | 72 | 100 (81) | 79 |
|  | QD-PP | 30 | CH₃OH | 10 | -27 | 72 | 100 (78) | 85 |
|  | QD-PP | 100 | CF₃CH₂OH | 10 | -27 | 12 | 100 (96) | 88 |
|  | QD-PP | 100 | CF₃CH₂OH | 10 | -27 | 12 | 100 (83) | 76 |
|  | QD-PP | 100 | CH₃OH | 10 | -27 | 12 | 100 (94) | 75 |
|  | QD-PP | 100 | CH₃OH | 10 | -27 | 36 | 100 (85) | 84 |

Figure 13

| Alcohol | Solvent | Reaction Time (h) | Conversion % (% Yield) | Ee (%) |
|---|---|---|---|---|
| $CF_3CH_2OH$ | Ether | 53 | 100 (98) | 89 |
| $CH_3OH$ | Ether | 13 | 82 | 86 |
| $CH_3OH$ | Toluene | 11 | 81 | 69 |

Figure 14

| Catalyst (mol%) | Alcohol (equiv) | Solvent | Reaction Time (min) | Conversion % (% Yield) | Ee (%) |
|---|---|---|---|---|---|
| 20 | 10 | Toluene | 40 | 87 | 56 |
| 100 | 10 | Toluene | 30 | 98 | 72 |
| 100 | 1 | Toluene | 90 | 93 | 82 |
| 100 | 1 | Ether | 90 | 92 | 83 |

Figure 15

| Catalyst (mol%) | Alcohol (equiv) | Solvent | Reaction Time (h) | Conversion % (% Yield) | Ee (%) |
|---|---|---|---|---|---|
| 100 | 10 | Toluene | 2 | 93 | 82 |
| 100 | 10 | Ether | 2 | 87 | 86 |
| 100 | 1 | Toluene | 20 | 96 | 91 |
| 100 | 1 | Ether | 20 | 96 | 91 |
| 50 | 1 | Ether | 101 | 89 | 85 |

Figure 16

| Catalyst (mol%) | Alcohol (equiv) | Solvent | Conversion % (% Yield) | Ee (%) |
|---|---|---|---|---|
| 100 | 1 | Ether | 93 | 90 |
| 100 | 1 | Toluene | 95 | 89 |

Figure 17

| Substrate (mmol) | Catalyst | Alcohol | Solvent | Reaction Time (h) | Conversion % (% Yield) | Ee (%) |
|---|---|---|---|---|---|---|
| 0.1 | QD-TB | MeOH | Ether | 49 | 95 | 88 |
| 0.05 | QD-TB | MeOH | Toluene | 11 | 82 | 78 |
| 0.1 | QD-TB | $CF_3CH_2OH$ | Ether | 13 | 100 (94) | 92 |
| 0.05 | Q-PP | MeOH | Ether | 75 | 91 | 75 |
| 0.05 | Q-PP | MeOH | Toluene | 49 | 96 | 50 |

CATALYTIC ASYMMETRIC DESYMMETRIZATION OF PROCHIRAL AND MESO COMPOUNDS

RELATED APPLICATIONS

This application is a continuation-in-part of U.S. patent application Ser. No. 10/366,581, filed Feb. 13, 2003; which is a continuation of U.S. patent application Ser. No. 09/825,167, filed Apr. 3, 2001; now U.S. Pat. No. 6,580,003 which claims the benefit of the filing date of U.S. Provisional Patent Application Ser. No. 60/194,520, filed Apr. 4, 2000.

GOVERNMENT SUPPORT

The invention was made with support provided by the National Institutes of Health (grant number GM-61591); therefore, the government has certain rights in the invention.

BACKGROUND OF THE INVENTION

The demand for enantiomerically pure compounds has grown rapidly in recent years. One important use for such chiral, non-racemic compounds is as intermediates for synthesis in the pharmaceutical industry. For instance, it has become increasingly clear that enantiomerically pure drugs have many advantages over racemic drug mixtures. These advantages (reviewed in, e.g., Stinson, S. C., *Chem Eng News*, Sept. 28, 1992, pp. 46–79) include the fewer side effects and greater potency often associated with enantiomerically pure compounds.

Traditional methods of organic synthesis were often optimized for the production of racemic materials. The production of enantiomerically pure material has historically been achieved in one of two ways: use of enantiomerically pure starting materials derived from natural sources (the so-called "chiral pool"); and the resolution of racemic mixtures by classical techniques. Each of these methods has serious drawbacks, however. The chiral pool is limited to compounds found in nature, so only certain structures and configurations are readily available. Resolution of racemates, which requires the use of resolving agents, may be inconvenient and time-consuming. Furthermore, resolution often means that the undesired enantiomer is discarded, thus decreasing efficiency and wasting half of the material.

SUMMARY OF THE INVENTION

One aspect of the present invention relates to a method of preparing a chiral, non-racemic compound from a prochiral substituted cyclic anhydride or a meso substituted cyclic anhydride, comprising the step of: reacting a prochiral substituted cyclic anhydride or a meso substituted cyclic anhydride with a nucleophile in the presence of a chiral, non-racemic tertiary amine catalyst; wherein said prochiral substituted cyclic anhydride or said meso substituted cyclic anhydride comprises an internal plane of symmetry or point of symmetry or both; wherein said meso substituted cyclic anhydride comprises at least two chiral centers; and wherein said nucleophile is an alcohol, thiol or amine; thereby producing a chiral, non-racemic compound.

In certain embodiments of the aforementioned method said prochiral substituted cyclic anhydride or meso substituted cyclic anhydride is a substituted succinic anhydride or a substituted glutaric anhydride.

In certain embodiments of the aforementioned method said nucleophile is an alcohol.

In certain embodiments of the aforementioned method said nucleophile is a primary alcohol.

In certain embodiments of the aforementioned method said nucleophile is methanol or $CF_3CH_2OH$.

In certain embodiments of the aforementioned method said chiral, non-racemic tertiary amine catalyst is Q-PP, Q-TB, QD-PP, QD-TB, $(DHQ)_2PHAL$, $(DHQD)_2PHAL$, $(DHQ)_2PYR$, $(DHQD)_2PYR$, $(DHQ)_2AQN$, $(DHQD)_2AQN$, DHQ-CLB, DHQD-CLB, DHQ-MEQ, DHQD-MEQ, DHQ-AQN, DHQD-AQN, DHQ-PHN, or DHQD-PHN.

In certain embodiments of the aforementioned method said chiral, non-racemic tertiary amine catalyst is DHQD-PHN or $(DHQD)_2AQN$.

In certain embodiments of the aforementioned method said chiral, non-racemic tertiary amine catalyst is Q-PP, Q-TB, QD-PP or QD-TB.

In certain embodiments of the aforementioned method said chiral, non-racemic tertiary amine catalyst is QD-PP.

In certain embodiments of the aforementioned method said prochiral substituted cyclic anhydride or meso substituted cyclic anhydride is a substituted succinic anhydride or substituted glutaric anhydride; said nucleophile is an alcohol; and said chiral, non-racemic tertiary amine catalyst is Q-PP, Q-TB, QD-PP, QD-TB, $(DHQ)_2PHAL$, $(DHQD)_2PHAL$, $(DHQ)_2PYR$, $(DHQD)_2PYR$, $(DHQ)_2AQN$, $(DHQD)_2AQN$, DHQ-CLB, DHQD-CLB, DHQ-MEQ, DHQD-MEQ, DHQ-AQN, DHQD-AQN, DHQ-PHN, or DHQD-PHN.

In certain embodiments of the aforementioned method said prochiral substituted cyclic anhydride or meso substituted cyclic anhydride is a substituted succinic anhydride or substituted glutaric anhydride; said nucleophile is a primary alcohol; and said chiral, non-racemic tertiary amine catalyst is Q-PP, Q-TB, QD-PP, QD-TB, $(DHQ)_2PHAL$, $(DHQD)_2PHAL$, $(DHQ)_2PYR$, $(DHQD)_2PYR$, $(DHQ)_2AQN$, $(DHQD)_2AQN$, DHQ-CLB, DHQD-CLB, DHQ-MEQ, DHQD-MEQ, DHQ-AQN, DHQD-AQN, DHQ-PHN, or DHQD-PHN.

In certain embodiments of the aforementioned method said prochiral substituted cyclic anhydride or meso substituted cyclic anhydride is a substituted succinic anhydride or substituted glutaric anhydride; said nucleophile is methanol or $CF_3CH_2OH$; and said chiral, non-racemic tertiary amine catalyst is Q-PP, Q-TB, QD-PP, QD-TB, $(DHQ)_2PHAL$, $(DHQD)_2PHAL$, $(DHQ)_2PYR$, $(DHQD)_2PYR$, $(DHQ)_2AQN$, $(DHQD)_2AQN$, DHQ-CLB, DHQD-CLB, DHQ-MEQ, DHQD-MEQ, DHQ-AQN, DHQD-AQN, DHQ-PHN, or DHQD-PHN.

In certain embodiments of the aforementioned method said prochiral substituted cyclic anhydride or meso substituted cyclic anhydride is a substituted succinic anhydride or substituted glutaric anhydride; said nucleophile is an alcohol; and said chiral, non-racemic tertiary amine catalyst is DHQD-PHN or $(DHQD)_2AQN$.

In certain embodiments of the aforementioned method said prochiral substituted cyclic anhydride or meso substituted cyclic anhydride is a substituted succinic anhydride or substituted glutaric anhydride; said nucleophile is a primary alcohol; and said chiral, non-racemic tertiary amine catalyst is DHQD-PHN or $(DHQD)_2AQN$.

In certain embodiments of the aforementioned method said prochiral substituted cyclic anhydride or meso substituted cyclic anhydride is a substituted succinic anhydride or substituted glutaric anhydride; said nucleophile is methanol or $CF_3CH_2OH$; and said chiral, non-racemic tertiary amine catalyst is DHQD-PHN or $(DHQD)_2AQN$.

In certain embodiments of the aforementioned method said prochiral substituted cyclic anhydride or meso substituted cyclic anhydride is a substituted succinic anhydride or substituted glutaric anhydride; said nucleophile is an alcohol; and said chiral, non-racemic tertiary amine catalyst is Q-PP, Q-TB, QD-PP or QD-TB.

In certain embodiments of the aforementioned method said prochiral substituted cyclic anhydride or meso substituted cyclic anhydride is a substituted succinic anhydride or substituted glutaric anhydride; said nucleophile is a primary alcohol; and said chiral, non-racemic tertiary amine catalyst is Q-PP, Q-TB, QD-PP or QD-TB.

In certain embodiments of the aforementioned method said prochiral substituted cyclic anhydride or meso substituted cyclic anhydride is a substituted succinic anhydride or substituted glutaric anhydride; said nucleophile is methanol or $CF_3CH_2OH$; and said chiral, non-racemic tertiary amine catalyst is Q-PP, Q-TB, QD-PP or QD-TB.

In certain embodiments of the aforementioned method said prochiral substituted cyclic anhydride or meso substituted cyclic anhydride is a substituted succinic anhydride or substituted glutaric anhydride; said nucleophile is an alcohol; and said chiral, non-racemic tertiary amine catalyst is QD-PP.

In certain embodiments of the aforementioned method said prochiral substituted cyclic anhydride or meso substituted cyclic anhydride is a substituted succinic anhydride or substituted glutaric anhydride; said nucleophile is a primary alcohol; and said chiral, non-racemic tertiary amine catalyst is QD-PP.

In certain embodiments of the aforementioned method said prochiral substituted cyclic anhydride or meso substituted cyclic anhydride is a substituted succinic anhydride or substituted glutaric anhydride; said nucleophile is methanol or $CF_3CH_2OH$; and said chiral, non-racemic tertiary amine catalyst is QD-PP.

In certain embodiments of the aforementioned method said chiral, non-racemic tertiary amine catalyst is present in less than about 30 mol % relative to said prochiral substituted cyclic anhydride or meso substituted cyclic anhydride.

In certain embodiments of the aforementioned method said chiral, non-racemic tertiary amine catalyst is present in less than about 20 mol % relative to said prochiral substituted cyclic anhydride or meso substituted cyclic anhydride.

In certain embodiments of the aforementioned method said chiral, non-racemic tertiary amine catalyst is present in less than about 10 mol % relative to said prochiral substituted cyclic anhydride or meso substituted cyclic anhydride.

In certain embodiments of the aforementioned method said chiral, non-racemic compound has an enantiomeric excess greater than about 50%.

In certain embodiments of the aforementioned method said chiral, non-racemic compound has an enantiomeric excess greater than about 70%.

In certain embodiments of the aforementioned method said chiral, non-racemic compound has an enantiomeric excess greater than about 90%.

In certain embodiments of the aforementioned method said chiral, non-racemic compound has an enantiomeric excess greater than about 95%.

BRIEF DESCRIPTION OF THE DRAWINGS

FIG. 13 depicts the results from desymmetrization of cis-2,3-dimethyl succinic anhydride. In each case: the amount of substrate was 0.1 mmol; the concentration of the substrate was 0.02 M; the catalyst was QD-PP; 20 mol % catalyst was used relative to the substrate; the amount of alcohol was 10 equiv; and the reaction was run at ambient temperature.

Figure 1:
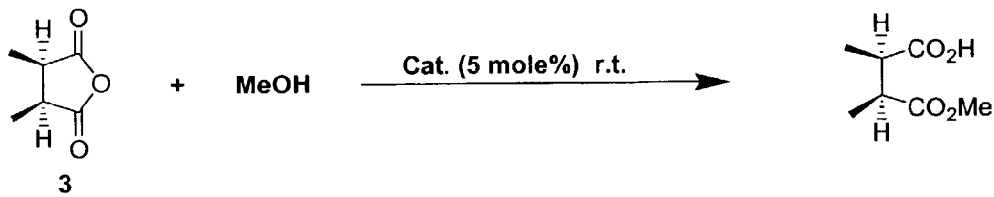
FIG. 1 presents the enantiomeric excess of the product obtained from the asymmetric desymmetrization of cis-2,3-dimethylsuccinic anhydride, as a function of the solvent and the catalyst used.

FIG. 14 depicts the results from desymmetrization of cis-2,3-dimethyl succinic anhydride. In each case: the amount of substrate was 0.1 mmol; the concentration of the substrate was 0.2 M; the catalyst was QD-PP; the alcohol was methanol; and the reaction was run at ambient temperature.

FIG. 15 depicts the results from desymmetrization of cis-2,3-dimethyl succinic anhydride. In each case: the amount of substrate was 0.1 mmol; the concentration of the substrate was 0.2 M; the catalyst was QD-PP; the alcohol was methanol; and the reaction was run at −25° C.

FIG. 16 depicts the results from desymmetrization of cis-2,3-dimethyl succinic anhydride. In each case: the amount of substrate was 0.2 mmol; the concentration of the substrate was 0.4 M; the catalyst was QD-PP; the alcohol was methanol; the reaction was run at −25° C.; and the reaction time was 6 hours.

FIG. 17 depicts the results from desymmetrization of cis-2,3-dimethyl succinic anhydride. In each case: the concentration of the substrate was 0.02 M; 20 mol % catalyst was used relative to the substrate; the amount of alcohol was 10 equiv; and the reaction was run at ambient temperature.

DETAILED DESCRIPTION OF THE INVENTION

The invention will now be described more fully with reference to the accompanying examples, in which certain preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

The ability to selectively transform a prochiral or meso compound to a enantiomerically enriched or enantiomerically pure chiral compound has broad application, especially in the agricultural and pharmaceutical industries, as well as in the polymer industry. As described herein, the present invention relates to methods and catalysts for the catalytic asymmetric desymmetrization of prochiral and meso compounds and the like. The primary constituents of the methods, which are set forth in detail below, are: a non-racemic chiral tertiary-amine-containing catalyst; a prochiral or meso substrate, typically a heterocycle comprising a pair of electrophilic atoms related by an internal plane or point of symmetry; and a nucleophile, typically the solvent, which under the reaction conditions selectively attacks one of the two aforementioned electrophilic atoms, generating an enantiomerically enriched chiral product. Additionally, the catalysts and methods of the present invention can be exploited to effect kinetic resolutions of racemic mixtures and the like.

Definitions

For convenience, certain terms employed in the specification, examples, and appended claims are collected here.

The term "nucleophile" is recognized in the art, and as used herein means a chemical moiety having a reactive pair of electrons. Examples of nucleophiles include uncharged compounds such as water, amines, mercaptans and alcohols, and charged moieties such as alkoxides, thiolates, carbanions, and a variety of organic and inorganic anions. Illustrative anionic nucleophiles include simple anions such as hydroxide, azide, cyanide, thiocyanate, acetate, formate or chloroformate, and bisulfite. Organometallic reagents such as organocuprates, organozincs, organolithiums, Grignard reagents, enolates, acetylides, and the like may, under appropriate reaction conditions, be suitable nucleophiles. Hydride may also be a suitable nucleophile when reduction of the substrate is desired.

The term "electrophile" is art-recognized and refers to chemical moieties which can accept a pair of electrons from a nucleophile as defined above. Electrophiles useful in the method of the present invention include cyclic compounds such as epoxides, aziridines, episulfides, cyclic sulfates, carbonates, lactones, lactams and the like. Non-cyclic electrophiles include sulfates, sulfonates (e.g. tosylates), chlorides, bromides, iodides, and the like The terms "electrophilic atom", "electrophilic center" and "reactive center" as used herein refer to the atom of the substrate which is attacked by, and forms a new bond to, the nucleophile. In most (but not all) cases, this will also be the atom from which the leaving group departs.

The term "electron-withdrawing group" is recognized in the art and as used herein means a functionality which draws electrons to itself more than a hydrogen atom would at the same position. Exemplary electron-withdrawing groups include nitro, ketone, aldehyde, sulfonyl, trifluoromethyl, —CN, chloride, and the like. The term "electron-donating group", as used herein, means a functionality which draws electrons to itself less than a hydrogen atom would at the same position. Exemplary electron-donating groups include amino, methoxy, and the like.

The terms "Lewis base" and "Lewis basic" are recognized in the art, and refer to a chemical moiety capable of donating a pair of electrons under certain reaction conditions. Examples of Lewis basic moieties include uncharged compounds such as alcohols, thiols, olefins, and amines, and charged moieties such as alkoxides, thiolates, carbanions, and a variety of other organic anions.

The terms "Lewis acid" and "Lewis acidic" are art-recognized and refer to chemical moieties which can accept a pair of electrons from a Lewis base.

The term "meso compound" is recognized in the art and means a chemical compound which has at least two chiral centers but is achiral due to an internal plane or point of symmetry.

The term "chiral" refers to molecules which have the property of non-superimposability on their mirror image partner, while the term "achiral" refers to molecules which are superimposable on their mirror image partner. A "prochiral molecule" is an achiral molecule which has the potential to be converted to a chiral molecule in a particular process.

The term "stereoisomers" refers to compounds which have identical chemical constitution, but differ with regard to the arrangement of their atoms or groups in space. In particular, the term "enantiomers" refers to two stereoisomers of a compound which are non-superimposable mirror images of one another. The term "diastereomers", on the other hand, refers to the relationship between a pair of stereoisomers that comprise two or more asymmetric centers and are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product. The subject method is said to produce a "stereoselectively-enriched" product (e.g., enantioselectively-enriched or diastereoselectively-enriched) when the yield of a particular stereoisomer of the product is greater by a statistically significant amount relative to the yield of that stereoisomer resulting from the same reaction run in the absence of a chiral catalyst. For example, an enantioselective reaction catalyzed by one of the subject chiral catalysts will yield an e.e. for a particular enantiomer that is larger than the e.e. of the reaction lacking the chiral catalyst.

The term "regioisomers" refers to compounds which have the same molecular formula but differ in the connectivity of the atoms. Accordingly, a "regioselective process" is one which favors the production of a particular regioisomer over others, e.g., the reaction produces a statistically significant preponderance of a certain regioisomer.

The term "reaction product" means a compound which results from the reaction of a nucleophile and a substrate. In general, the term "reaction product" will be used herein to refer to a stable, isolable compound, and not to unstable intermediates or transition states.

The term "substrate" is intended to mean a chemical compound which can react with a nucleophile, or with a ring-expansion reagent, according to the present invention, to yield at least one product having a stereogenic center.

The term "catalytic amount" is recognized in the art and means a substoichiometric amount relative to a reactant. As used herein, a catalytic amount means from 0.0001 to 90 mole percent relative to a reactant, more preferably from 0.001 to 50 mole percent, still more preferably from 0.01 to 10 mole percent, and even more preferably from 0.1 to 5 mole percent relative to a reactant.

As discussed more fully below, the reactions contemplated in the present invention include reactions which are enantioselective, diastereoselective, and/or regioselective. An enantioselective reaction is a reaction which converts an achiral reactant to a chiral product enriched in one enantiomer. Enantioselectivity is generally quantified as "enantiomeric excess" (ee) defined as follows:

% Enantiomeric Excess $A$ $(ee)$=(% Enantiomer $A$)−(% Enantiomer $B$)

where A and B are the enantiomers formed. Additional terms that are used in conjunction with enatioselectivity include "optical purity" or "optical activity". An enantioselective reaction yields a product with an e.e. greater than zero. Preferred enantioselective reactions yield a product with an e.e. greater than 20%, more preferably greater than 50%, even more preferably greater than 70%, and most preferably greater than 80%.

A diastereoselective reaction converts a chiral reactant (which may be racemic or enantiomerically pure) to a product enriched in one diastereomer. If the chiral reactant is racemic, in the presence of a chiral non-racemic reagent or catalyst, one reactant enantiomer may react more slowly than the other. This class of reaction is termed a kinetic resolution, wherein the reactant enantiomers are resolved by differential reaction rate to yield both enantiomerically-enriched product and enantiomerically-enriched unreacted substrate. Kinetic resolution is usually achieved by the use of sufficient reagent to react with only one reactant enantiomer (i.e. one-half mole of reagent per mole of racemic substrate). Examples of catalytic reactions which have been used for kinetic resolution of racemic reactants include the Sharpless epoxidation and the Noyori hydrogenation.

A regioselective reaction is a reaction which occurs preferentially at one reactive center rather than another non-identical reactive center. For example, a regioselective reaction of an unsymmetrically substituted epoxide substrate would involve preferential reaction at one of the two epoxide ring carbons.

The term "non-racemic" with respect to the chiral catalyst, means a preparation of catalyst having greater than 50% of a given enantiomer, more preferably at least 75%. "Substantially non-racemic" refers to preparations of the catalyst which have greater than 90% ee for a given enantiomer of the catalyst, more preferably greater than 95% ee.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 of fewer. Likewise, preferred cycloalkyls have from 4–10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths.

The terms "alkenyl" and "alkynyl" refer to unsaturated aliphatic groups analogous in length and possible substitution to the alkyls described above, but which contain at least one double or triple carbon-carbon bond, respectively.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

As used herein, the term "amino" means —$NH_2$; the term "nitro" means —$NO_2$; the term "halogen" designates —F, —Cl, —Br or —I; the term "thiol" means —SH; the term "hydroxyl" means —OH; the term "sulfonyl" means —$SO_2$—; and the term "organometallic" refers to a metallic atom (such as mercury, zinc, lead, magnesium or lithium) or a metalloid (such as silicon, arsenic or selenium) which is bonded directly to a carbon atom, such as a diphenylmethylsilyl group.

The terms "amine" and "amino" are art-recognized and refer to both unsubstituted and substituted amines, e.g., a moiety that can be represented by the general formula:

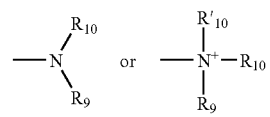

wherein $R_9$, $R_{10}$ and $R'_{10}$ each independently represent a group permitted by the rules of valence.

The term "acylamino" is art-recognized and refers to a moiety that can be represented by the general formula:

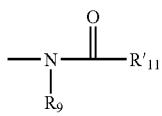

wherein $R_9$ is as defined above, and $R'_{11}$ represents a hydrogen, an alkyl, an alkenyl or $-(CH_2)_m-R_8$, where m and $R_8$ are as defined above.

The term "amido" is art recognized as an amino-substituted carbonyl and includes a moiety that can be represented by the general formula:

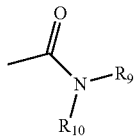

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m-R_8$, wherein m and $R_8$ are defined above. Representative alkylthio groups include methylthio, ethyl thio, and the like.

The term "carbonyl" is art recognized and includes such moieties as can be represented by the general formula:

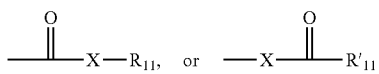

wherein X is a bond or represents an oxygen or a sulfur, and $R_{11}$ represents a hydrogen, an alkyl, an alkenyl, $-(CH_2)_m-R_8$ or a pharmaceutically acceptable salt, $R'_{11}$ represents a hydrogen, an alkyl, an alkenyl or $-(CH_2)_m-R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The term "sulfonate" is art recognized and includes a moiety that can be represented by the general formula:

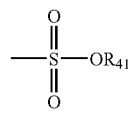

in which $R_{41}$ is an electron pair, hydrogen, alkyl, cycloalkyl, or aryl.

The term "sulfonylamino" is art recognized and includes a moiety that can be represented by the general formula:

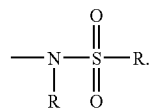

The term "sulfamoyl" is art-recognized and includes a moiety that can be represented by the general formula:

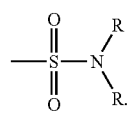

The term "sulfonyl", as used herein, refers to a moiety that can be represented by the general formula:

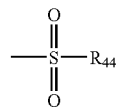

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

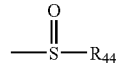

in which $R_{44}$ is selected from the group consisting of hydrogen, alkyl, alkenyl, alkynyl, cycloalkyl, heterocyclyl, aralkyl, or aryl.

The term "sulfate", as used herein, means a sulfonyl group, as defined above, attached to two hydroxy or alkoxy groups. Thus, in a preferred embodiment, a sulfate has the structure:

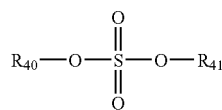

in which $R_{40}$ and $R_{41}$ are independently absent, a hydrogen, an alkyl, or an aryl. Furthermore, $R_{40}$ and $R_{41}$, taken together with the sulfonyl group and the oxygen atoms to which they are attached, may form a ring structure having from 5 to 10 members.

Analogous substitutions can be made to alkenyl and alkynyl groups to produce, for example, alkenylamines, alkynylamines, alkenylamides, alkynylamides, alkenylimines, alkynylimines, thioalkenyls, thioalkynyls, carbonyl-substituted alkenyls or alkynyls, alkenoxyls, alkynoxyls, metalloalkenyls and metalloalkynyls.

The term "aryl" as used herein includes 4-, 5-, 6- and 7-membered single-ring aromatic groups which may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycle". The aromatic ring can be substituted at one or more ring positions with such substituents as described above, as for example, halogens, alkyls, alkenyls, alkynyls, hydroxyl, amino, nitro, thiolamines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —CN, or the like.

The terms "heterocycle" or "heterocyclic group" refer to 4 to 10-membered ring structures, more preferably 5 to 7 membered rings, which ring structures include one to four heteroatoms. Heterocyclic groups include pyrrolidine, oxolane, thiolane, imidazole, oxazole, piperidine, piperazine, morpholine. The heterocyclic ring can be substituted at one or more positions with such substituents as described above, as for example, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —CN, or the like.

The terms "polycycle" or "polycyclic group" refer to two or more cyclic rings (e.g., cycloalkyls, cycloalkenyls, cycloalkynyls, aryls and/or heterocycles) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, or —$(CH_2)_m$—$R_7$, —$CF_3$, —CN, or the like.

The term "heteroatom" as used herein means an atom of any element other than carbon or hydrogen. Preferred heteroatoms are nitrogen, oxygen, sulfur, phosphorus and selenium.

For purposes of this invention, the chemical elements are identified in accordance with the Periodic Table of the Elements, CAS version, Handbook of Chemistry and Physics, 67th Ed., 1986–87, inside cover.

The terms ortho, meta and para apply to 1,2-, 1,3- and 1,4-disubstituted benzenes, respectively. For example, the names 1,2-dimethylbenzene and ortho-dimethylbenzene are synonymous.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms, represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations. The abbreviations contained in said list, and all abbreviations utilized by organic chemists of ordinary skill in the art are hereby incorporated by reference.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis, $2^{nd}$* ed.; Wiley: New York, 1991).

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Catalysts of the Invention

The catalysts employed in the subject methods are non-racemic chiral amines which present an asymmetric environment, causing differentiation between two or more moieties related by symmetry in a prochiral or meso molecule, i.e., a molecule comprising at least two chiral centers, and an internal plane or point of symmetry or both. In general, catalysts intended by the present invention can be characterized in terms of a number of features. For instance, a salient aspect of each of the catalysts contemplated by the instant invention concerns the use of asymmetric bicyclic or polycyclic scaffolds incorporating the tertiary amine moiety which provide a rigid or semi-rigid environment near the amine nitrogen. This feature, through imposition of structural rigidity on the amine nitrogen in proximity to one or more asymmetric centers present in the scaffold, contributes to the creation of a meaningful difference in the energies of the corresponding diastereomeric transitions states for the overall transformation. Furthermore, the choice of substituents may also effect catalyst reactivity. For example, bulkier substituents on the catalyst are generally found to provide higher catalyst turnover numbers.

A preferred embodiment for each of the embodiments described above provides a catalyst having a molecular weight less than 2,000 g/mol, more preferably less than 1,000 g/mol, and even more preferably less than 500 g/mol. Additionally, the substituents on the catalyst can be selected to influence the solubility of the catalyst in a particular solvent system.

In certain embodiments, the chiral, non-racemic tertiary amine catalyst comprises a 1-azabicyclo[2.2.2]octane moiety or a 1,4-diazabicyclo[2.2.2]octane moiety. In certain embodiments, the chiral, non-racemic tertiary amine catalyst is a cinchona alkaloid, Q-PP, Q-TB, QD-PP, QD-TB, (DHQ)$_2$PHAL, (DHQD)$_2$PHAL, (DHQ)$_2$PYR, (DHQD)$_2$PYR, (DHQ)$_2$AQN, (DHQD)$_2$AQN, DHQ-CLB, DHQD-CLB, DHQ-MEQ, DHQD-MEQ, DHQ-AQN, DHQD-AQN, DHQ-PHN, or DHQD-PHN. In certain embodiments, the chiral, non-racemic tertiary amine catalyst is DHQD-PHN or (DHQD)$_2$AQN. In certain embodiments, the chiral, non-racemic tertiary amine catalyst is Q-PP, Q-TB, QD-PP or QD-TB. In certain embodiments, the chiral, non-racemic tertiary amine catalyst is QD-PP.

As mentioned briefly above, the choice of catalyst substituents can also effect the electronic properties of the catalyst. Substitution of the catalyst with electron-rich (electron-donating) moieties (including, for example, alkoxy or amino groups) may increase the electron density of the catalyst at the tertiary amine nitrogen, rendering it a stronger nucleophile and/or Bronsted base and/or Lewis base. Conversely, substitution of the catalyst with electron-poor moieties (for example, chloro or trifluoromethyl groups) can result in lower electron density of the catalyst at the tertiary amine nitrogen, rendering it a weaker nucleophile and/or Bronsted base and/or Lewis base. To summarize this consideration, the electron density of the catalyst can be important because the electron density at the tertiary amine nitrogen will influence the Lewis basicity of the nitrogen and its nucleophilicity. Choice of appropriate substituents thus makes possible the "tuning" of the reaction rate and the stereoselectivity of the reaction.

Methods of the Invention—Preparation of Asymmetric Tertiary Amine-Containing Catalysts Certain aspects of the present invention relate to methods for preparing tertiary amines, which tertiary amine will be useful in the desymmetrization methods of the present invention. In certain embodiments, the tertiary amines are synthesized according to a general procedure, wherein a diamine is reacted with two equivalents of a chiral, non-racemic glycidyl sulfonate or halide. For example, the scheme below depicts an embodiment of these methods, wherein ethylene diamine and two equivalents of a chiral, non-racemic glycidyl nosylate react to give a chiral, non-racemic bis-tertiary amine. See also Example 2.

enantiomer can be substantially reduced or eliminated altogether.

In general, the invention features a stereoselective ring opening process which comprises combining a nucleophilic reactant, a prochiral, meso or chiral cyclic substrate, and at least a catalytic amount of non-racemic chiral catalyst of particular characteristics (as described herein). The cyclic substrate of the reaction will include a carbocycle or heterocycle comprising an electrophilic atom susceptible to attack by the nucleophile. The combination is maintained under conditions appropriate for the chiral catalyst to catalyze stereoselective opening of the cyclic substrate at the electrophilic atom by reaction with the nucleophilic reactant. This reaction can be applied to enantioselective processes as well as diastereoselective processes. It may also be adapted for regioselective reactions. Examples of enantioselective reactions, kinetic resolutions, and regioselective reactions which may be catalyzed according to the present invention follow.

In another aspect of the present invention, kinetic resolution of enantiomers occurs by catalysis, using a subject chiral catalyst, of the tranformation of a racemic substrate. In the subject kinetic resolution processes for a racemic substrate, one enantiomer can be recovered as unreacted substrate while the other is transformed to the desired product. Of course, it will be appreciated that the kinetic resolution can be performed by removing the undesired enantiomer by reaction with a nucleophile, and recovering the desired enantiomer unchanged from the reaction mixture. One significant advantage of this approach is the ability to use inexpensive racemic starting materials rather than the expensive, enantiomerically pure starting materials. In certain embodiments, the subject catalysts may be used in kinetic resolutions of racemic cyclic substrates wherein the nucleophile is a co-solvent. Suitable nucleophiles of this type include water, alcohols, and thiols.

The methods of this invention can provide optically active products with very high stereoselectivity (e.g., enantioselectivity or diastereoselectivity) or regioselectivity. In preferred embodiments of the subject desymmetrization reactions, products with enantiomeric excesses of greater than about 50%, greater than about 70%, greater than about 90%,

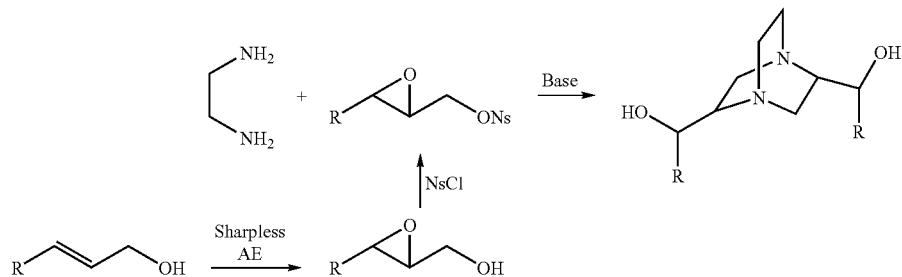

Methods of the Invention—Catalyzed Reactions

In one aspect of the present invention, there is provided a method for stereoselectively producing compounds with at least one stereogenic center from prochiral or meso starting materials. An advantage of this invention is that enantiomerically enriched products can be synthesized from prochiral or racemic reactants. Another advantage is that yield losses associated with the production of an undesired and most preferably greater than about 95% can be obtained. The methods of the invention may also be carried out under reaction conditions suitable for commercial use, and, typically, proceed at reaction rates suitable for large scale operations.

In certain embodiments, the chiral, non-racemic tertiary amine catalyst is present in less than about 30 mol % relative to the prochiral starting material. In certain embodiments, the chiral, non-racemic tertiary amine catalyst is present in less than about 20 mol % relative to the prochiral starting material. In certain embodiments, the chiral, non-racemic tertiary amine catalyst is present in less than about 10 mol % relative to the prochiral starting material. In certain embodiments, the chiral, non-racemic tertiary amine catalyst is present in less than about 5 mol % relative to the prochiral starting material.

As is clear from the above discussion, the chiral products produced by the asymmetric synthesis methods of this invention can undergo further reaction(s) to afford desired derivatives thereof. Such permissible derivatization reactions can be carried out in accordance with conventional procedures known in the art. For example, potential derivatization reactions include esterification, N-alkylation of amides, and the like. The invention expressly contemplates the preparation of end-products and synthetic intermediates which are useful for the preparation or development or both of cardiovascular drugs, non-steroidal anti-inflammatory drugs, central nervous system agents, and antihistaminics.

Nucleophiles

Nucleophiles which are useful in the present invention may be determined by the skilled artisan. It will be understood that while undesirable side reactions (such as catalyst degradation) may occur, the rates of such reactions can be rendered slow—through the selection of reactants and conditions—in comparison with the rate of the desired reaction(s).

Nucleophiles can be chosen for each substrate and will vary according to the substrate structure and the desired product. Routine experimentation may be necessary to determine the preferred nucleophile for a given transformation. For example, if a nitrogen-containing nucleophile is desired, it may be selected from ammonia, phthalimide, hydrazine, an amine or the like. Similarly, oxygen nucleophiles such as water, hydroxide, alcohols, alkoxides, siloxanes, carboxylates, or peroxides may be used to introduce oxygen; and mercaptans, thiolates, bisulfite, thiocyanate and the like may be used to introduce a sulfur-containing moiety. Additional nucleophiles will be apparent to those of ordinary skill in the art.

For nucleophiles which exist as anions, the counterion can be any of a variety of conventional cations, including alkali and alkaline earth metal cations and ammonium cations.

In certain embodiments, the nucleophile may be part of the substrate, resulting in an intramolecular reaction.

Substrates

As discussed above, a wide variety of substrates are useful in the methods of the present invention. The choice of substrate will depend on a number of factors, such as the nucleophile to be employed and the desired product, and an appropriate substrate will be apparent to the skilled artisan. It will be understood that the substrate preferably will not contain any interfering functionalities. In general, an appropriate substrate, e.g., a prochiral or meso compound, will contain at least a pair of reactive electrophilic centers or moieties related by an internal plane or point of symmetry at which a nucleophile attacks with the assistance of the catalyst. The catalyzed, stereoselective attack of the nucleophile at one of these electrophilic centers will produce a chiral, non-racemic product.

Most of the substrates contemplated for use in the methods of the present invention contain at least one ring having three to seven atoms. Small rings are frequently strained, enhancing their reactivity. However, in some embodiments a cyclic substrate may not be strained, i.e., it may comprise a larger ring with electrophilic centers. Examples of suitable cyclic substrates which can be opened in the subject method include cyclic anhydrides, cyclic imides, and the like.

In preferred embodiments, the cyclic substrate is a prochiral or meso compound. In other embodiments, for example, kinetic resolutions, the cyclic substrate will be a chiral compound. In certain embodiments, the substrate will be a racemic mixture. In certain embodiments, the substrate will be a mixture of diastereomers.

In preferred embodiments, the electrophilic atom is carbon, e.g., the carbon of a carbonyl moiety comprised by an anhydride or imide. However, in certain embodiments, the electrophilic atom may be a heteroatom.

Reaction Conditions

The asymmetric reactions of the present invention may be performed under a wide range of conditions, although it will be understood that the solvents and temperature ranges recited herein are not limitative and only correspond to a preferred mode of the methods of the invention.

In general, it will be desirable that reactions are run using mild conditions which will not adversely effect the substrate, the catalyst, or the product. For example, the reaction temperature influences the speed of the reaction, as well as the stability of the reactants, products, and catalyst. The reactions will usually be run at temperatures in the range of $-78°$ C. to $100°$ C., more preferably in the range $-30°$ C. to $30°$ C. and still more preferably in the range $-30°$ C. to $0°$ C.

In general, the asymmetric synthesis reactions of the present invention are carried out in a liquid reaction medium. However, the reactions may be run without addition of solvent. Alternatively, the reactions may be run in an inert solvent, preferably one in which the reaction ingredients, including the catalyst, are substantially soluble. Suitable solvents include ethers such as diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents. Furthermore, in certain embodiments, it may be advantageous to employ a solvent which is not inert to the substrate under the conditions employed, e.g., use of ethanol as a solvent when ethanol is the desired nucleophile. In embodiments where water or hydroxide are not preferred nucleophiles, the reactions can be conducted under anhydrous conditions. In certain embodiments, ethereal or aromatic hydrocarbon solvents are preferred. In certain preferred embodiments, the solvent is diethyl ether or toluene. In embodiments where water or hydroxide are preferred nucleophiles, the reactions may be run in solvent mixtures comprising an appropriate amount of water and/or hydroxide.

The invention also contemplates reaction in a biphasic mixture of solvents, in an emulsion or suspension, or reaction in a lipid vesicle or bilayer. In certain embodiments, it may be preferred to perform the catalyzed reactions on the solid phase. Further, in some preferred embodiments, the reaction may be carried out under an atmosphere of a reactive gas. For example, desymmetrization with cyanide as nucleophile may be performed under an atmosphere of HCN gas. The partial pressure of the reactive gas may be from 0.1 to 1000 atmospheres, more preferably from 0.5 to 100 atm, and most preferably from about 1 to about 10 atm. On the other hand, in certain embodiments it is preferable to perform the reactions under an inert atmosphere of a gas such as nitrogen or argon.

The asymmetric synthesis methods of the present invention can be conducted in continuous, semi-continuous or batch fashion and may involve a liquid recycle and/or gas recycle operation as desired. However, the methods of this invention are preferably conducted in batch fashion. Likewise, the manner or order of addition of the reaction ingredients, catalyst and solvent are also not critical and may be accomplished in any conventional fashion.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the optically active metal-ligand complex catalyst. When complete conversion is not desired or not obtainable, the starting materials can be separated from the product and then recycled back into the reaction zone.

The methods may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, the chiral catalyst may be immobilized or incorporated into a polymer or other insoluble matrix by, for example, covalently linking it to the polymer or solid support through one or more of its substituents. An immobilized catalyst may be easily recovered after the reaction, for instance, by filtration or centrifugation. Further, the substrate or nucleophile may be immobilized or incorporated into a polymer or other insoluble matrix by, for example, covalently linking it to the polymer or solid support through one or more of its substituents. Such an approach may form the basis for the preparation of a combinatorial library of compounds tethered to a solid support.

EXEMPLIFICATION

The invention now being generally described, it will be more readily understood by reference to the following examples which are included merely for purposes of illustration of certain aspects and embodiments of the present invention, and are not intended to limit the invention.

Example 1

Highly Enantioselective Catalytic Desymmetrization of Cyclic meso Anhydrides

Enantioselective opening of the readily accessible meso-cyclic anhydrides generates enantiomerically enriched chiral hemiesters containing one or multiple stereogenic centers and two chemically differentiated carbonyl functionalities (eq. 1). These optically active bifunctional hemiesters are versatile chiral building blocks in asymmetric synthesis.[1,2,3,4,5,6,7,8,9] Due to its great significance for organic synthesis, the development of highly enantioselective desymmetrization of meso-cyclic anhydrides has been a topic of intense research.[10,11,12,13,14,15] Synthetically useful selectivity has been obtained in desymmetrizations assisted by a stoichiometric amount of chiral auxiliaries or chiral mediators.[10,11] Despite considerable efforts,[11-15] the development of a general and effective catalytic desymmetrization of meso-cyclic anhydrides has not yet been achieved and therefore remains a desirable and highly challenging goal.

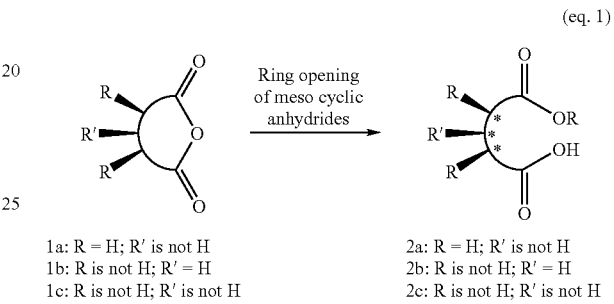

(eq. 1)

1a: R = H; R' is not H
1b: R is not H; R' = H
1c: R is not H; R' is not H

2a: R = H; R' is not H
2b: R is not H; R' = H
2c: R is not H; R' is not H

Our general interests in asymmetric catalysis of chiral Lewis bases lead our attention to amine-catalyzed alcoholysis of cyclic anhydride. Oda first reported that cinchona alkaloids catalyze asymmetric methanolysis of various mono and bicyclic anhydrides.[12] Atkin later extended this reaction to desymmetrize certain tricyclic anhydrides.[13] Although the reactions proceeded in good yield, the hemiesters were obtained in low to modest enantiomeric excess. We suspect that the unsatisfactory enantioselectivity may partially arise from the existence of a non-selective catalysis by the quinoline nitrogen since the monohydrochloride quinine is reported by Atkin to catalyze the methanolysis of the cyclic anhydride with no enantioselectivity.[13a] This quinoline nitrogen-catalyzed racemic pathway should become increasingly competitive as the reaction proceeds to high conversion when the rate of the quinuclidine nitrogen-catalyzed enantioselective reaction is expected to reduce significantly as a result of deactivation of the catalyst caused by protonation of the quinuclidine nitrogen by the acidic hemiester. In principle the racemic pathway could be suppressed by using analogs of cinchona alkaloids devoid of the quinoline nitrogen as the catalyst. The implementation of such an approach is, however, experimentally difficult due to the considerable synthetic effort required for the preparation of such analogs.[16] Furthermore, a large, if not stoichiometric, amount of the quinuclidine catalysts may be required to promote the reaction to go to completion. We are interested in exploring an alternative strategy of decreasing the basicity of the quinuclidine nitrogen, thereby shifting the equilibrium of the acid-base reaction towards the formation of the free amine catalyst. Such a strategy could lead to significant improvements in both the efficiency and the selectivity of the asymmetric catalysis through minimizing the deactivation of the free base amine catalyst by the acidic hemiester. Furthermore this approach could be easily implemented experimentally by changing the environment around the quinuclidine nitrogen via a simple modification of the cinchona alkaloid. We envisaged that a straightforward derivatizations of the C-9 alcohol with bulky alkyl or aryl groups could generate ethers of cinchona alkaloids with a decreased basicity of the quinuclidine nitrogen by destabilizing the ammonium ion x via the creation of a steric barrier for ion solvation. To this end, following the condition reported by Oda,[12] a variety of commercially available aryl ethers and esters of cinchona alkaloids are screened for their ability to catalyze enantioselective methanolysis of 2,3-dimethyl succinic anhydride (3). The results of our screening study are described in FIG. 1.

We were pleased to find that very good enantioselectivity is obtained with reactions mediated by aryl ethers of both a monocinchona (DHQD.PHN) and a biscinchona alkaloids [(DHQD)$_2$AQN].[17] While both alkaloids are effective catalyst, the latter in general gives higher enantioselectivity. When one equivalent of anhydride 3 was treated with 10 equivalent of methanol in dry toluene in the presence of 5 mol % of either DHQD.PHN or (DHQD)$_2$AQN as catalyst, the reaction went to completion in 2–4 hours to give the corresponding hemiester in 81% and 85% ee respectively. The structure of the aryl group of the modified cinchona alkaloids has a dramatic impact on the selectivity of the catalyst. While catalysts bearing bulky aromatic groups such as PHN and AQN afford high enantioselectivities, a dramatic deterioration in enantioselectivity was observed with catalysts bearing relatively small heterocyclic rings as substituents at O-9 position (entries 2, 3, 6, 7 in FIG. 1). The reaction can be further optimized to give the product in excellent ee (93% ee) at room temperature by using ether as the solvent.

Figure 2:
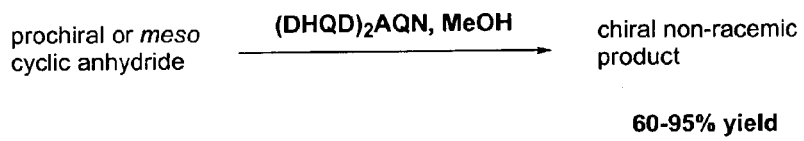
FIG. 2 presents the enantiomeric excesses of the products obtained from the asymmetric desymmetrization of various meso cyclic anhydrides, as a function of the reaction conditions used. The absolute configuration of each product was determined by comparison to an authentic sample. Enantiomeric excesses were determined using chiral GC or literature methods. In Entries 1–3, the enantiomeric excesses in parentheses pertain to products of the opposite absolute configuration obtained using $(DHQ)_2AQN$ as the catalyst. In Entry 4, $(DHQD)_2PHAL$ was used as the catalyst.
Figure 3:
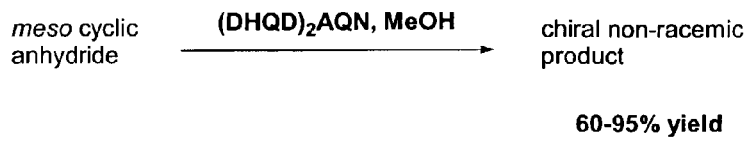
FIG. 3 presents the enantiomeric excesses of the products obtained from the asymmetric desymmetrization of various meso cyclic anhydrides, as a function of the reaction conditions used. The absolute configuration of each product was determined by comparison to an authentic sample. Enantiomeric excesses were determined using chiral GC or literature methods. In Entries 7 and 8, $(DHQD)_2PHAL$ was used as the catalyst.
Figure 4:
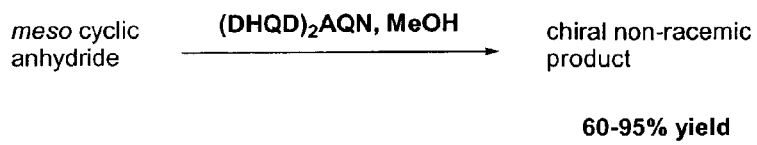
FIG. 4 presents the enantiomeric excesses of the products obtained from the asymmetric desymmetrization of various meso cyclic anhydrides, as a function of the reaction conditions used. The absolute configuration of each product was determined by comparison to an authentic sample. Enantiomeric excesses were determined using chiral GC or literature methods. In Entries 9 and 11, $(DHQD)_2PHAL$ was used as the catalyst.
Figure 5:
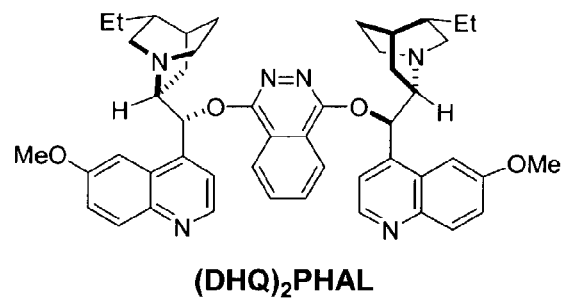
FIG. 5 depicts the structures of certain catalysts used in the methods of the present invention, and the abbreviations used herein for them.
Figure 5:
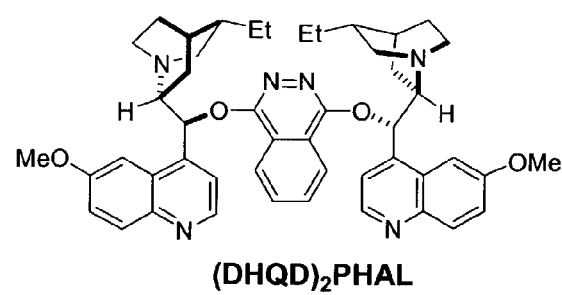
Figure 5:
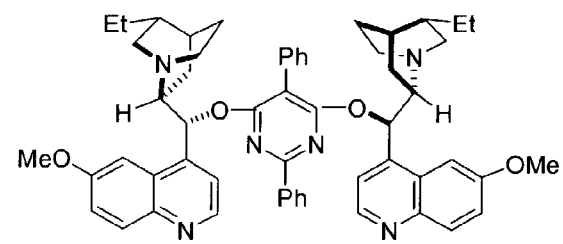
Figure 5:
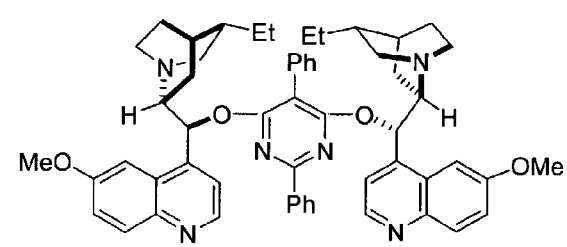
Figure 5:
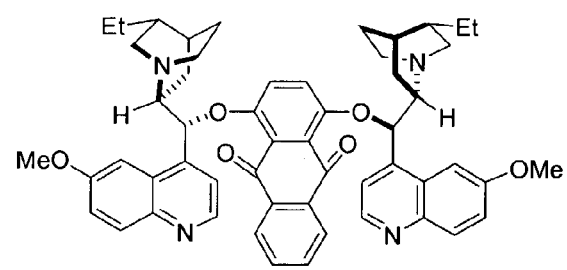
Figure 5:
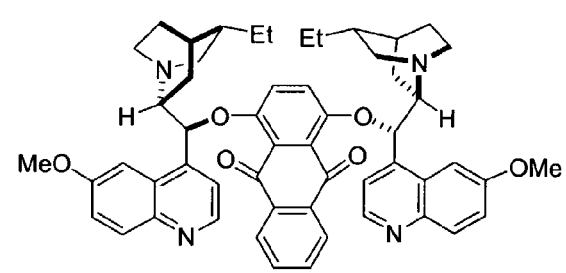
Figure 6:
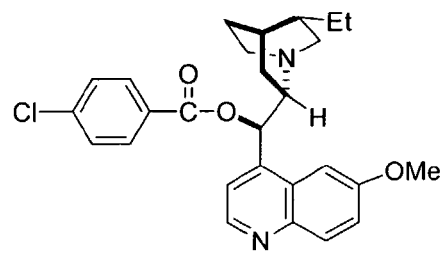
FIG. 6 depicts the structures of certain catalysts used in the methods of the present invention, and the abbreviations used herein for them.
Figure 6:
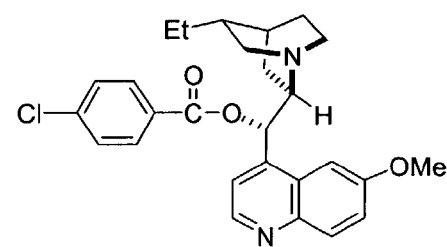
Figure 6:
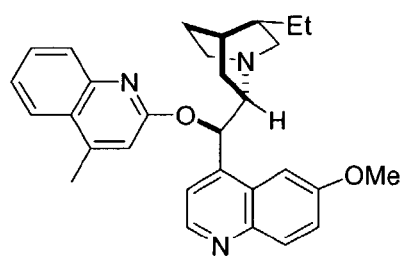
Figure 6:
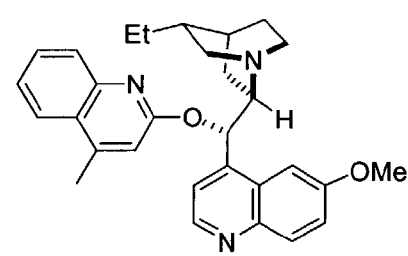
Figure 6:
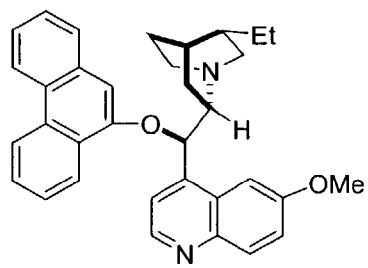
Figure 6:
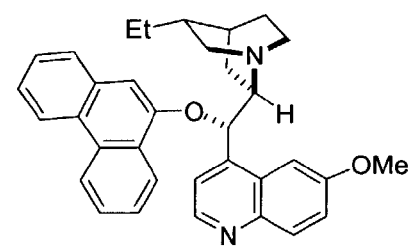
Figure 6:
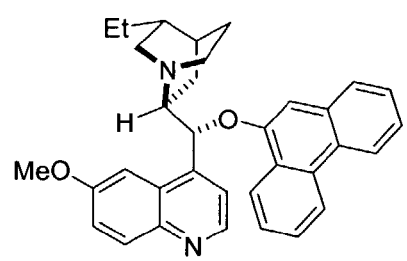
Figure 6:
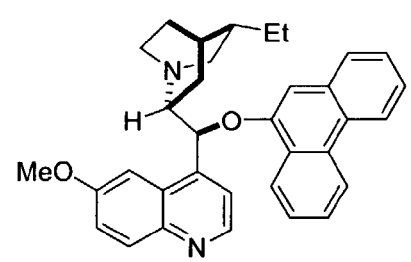
Figure 7:
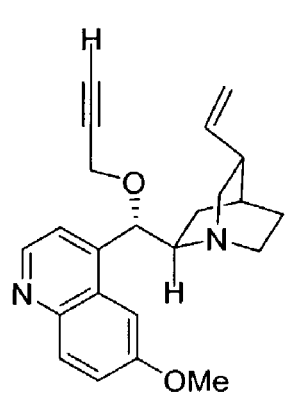
FIG. 7 depicts the structures of certain catalysts used in the methods of the present invention, and the abbreviations used herein for them.
Figure 7:
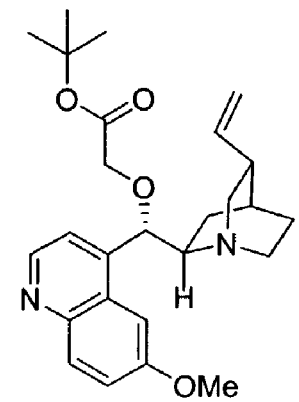
Figure 7:
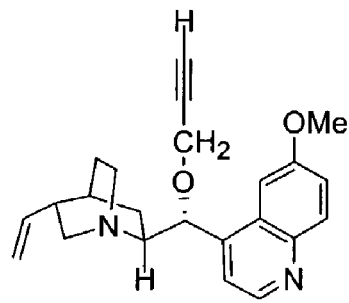
Figure 7:
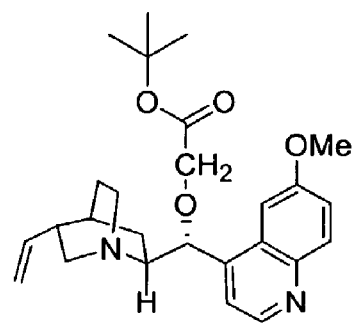
Figure 8:
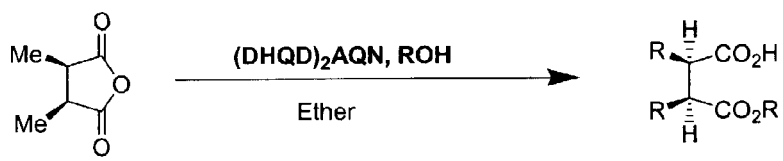
FIG. 8 depicts the enantiomeric excesses of the products obtained from the asymmetric desymmetrization of various meso cyclic anhydrides, as a function of the reaction conditions used.
Figure 9:
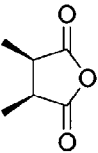
FIG. 9 depicts the enantiomeric excesses of the products obtained from the asymmetric desymmetrization of various meso cyclic anhydrides, as a function of the reaction conditions used. The absolute configuration of each product was determined by comparison to an authentic sample. Enantiomeric excesses were determined using chiral GC or literature methods.
Figure 9:
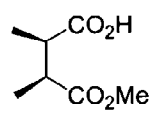
Figure 9:
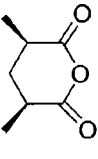
Figure 9:
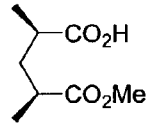
Figure 9:
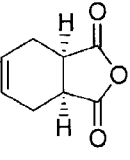
Figure 9:
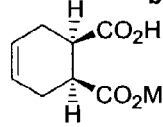
Figure 9:
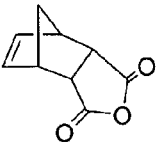
Figure 9:
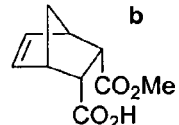
Figure 10:
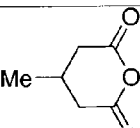
FIG. 10 depicts the results from desymmetrization of a number of prochiral cyclic anhydrides. In each case: the amount of substrate was 0.1 mmol; the concentration of the substrate was 0.2 M; 110 mol % catalyst was used relative to the substrate; the amount of alcohol was 1.5 equiv; the solvent was toluene; and the reaction temperature was −43° C.
Figure 10:
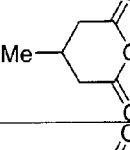
Figure 10:
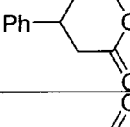
Figure 10:
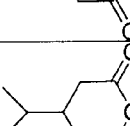
Figure 10:
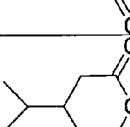
Figure 10:
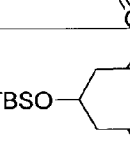
Figure 10:
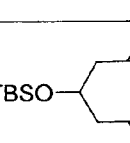
Figure 10:

Encouraged by these promising results, we investigated the catalytic desymmetrization of a wide variety of cyclic anhydrides. The results are summarized in FIGS. 2–4. The scope of the reaction is very general in giving excellent enantioselectivity and yield for the desymmetrization of a wide range of meso-cyclic anhydrides. Extraordinarily high enantioselectivity was observed for anhydride 3 as well as each of the bicyclic anhydrides employed in our investigation (entries 1, 5, 6 and 7 in FIGS. 2–4). Excellent enantioselectivities are obtained with monocyclic and tricyclic anhydrides (entries 2, 3, 8, 9, 10, and 11 in FIGS. 2–4) to give acyclic and bicyclic chiral hemiesters respectively in highly enantiomerically enriched form. Substrates containing heterocyclic rings other than the cyclic anhydride are also converted into the desired product in very high enantioselectivity (entries 10 and 11 in FIGS. 2–4). It is remarkable that even a monocyclic anhydride with a β-methyl substituent is transformed in 89% ee although a relatively high catalyst loading is required. The high enantioselectivity in the ring opening of 1,2-cyclopentylanhydride (entry 5 in FIGS. 2–4) is particularly noteworthy considering that it is significantly higher than that obtained by reactions using stoichiometric amount of chiral promoters.[11] Furthermore, synthetic routes based on hydrolytic enzymes can only provide the cyclopentyl hemiester in low ee. It is significant to note that when (DHQ)$_2$AQN was employed to catalyze the ring opening of 2,3-dimethylsuccinic anhydride (3) the opposite enantiomer of the corresponding hemiester was obtained in 96% ee, thus proving that either enantiomers of the hemiesters can be prepared in a straightforward and highly enantioselective fashion via the reaction described here. We are surprised to find that (DHQD)$_2$AQN-mediated ring opening of 2,4-dimethylglutaricanhydride gives the desired hemiester in good yield but in very low ee (30% ee). The enantioselectivity can, however, be improved significantly when the reaction is promoted by (DHQD)$_2$PHAL (entry 4 in FIGS. 2–4).

We have performed a preparative scale reaction to demonstrate the practicality of this catalytic desymmetrization. Anhydride 3 was transformed on a 5 mmol scale to the corresponding hemiester in larger than 98% ee with a catalyst loading of 5 mol %. When the starting material was consumed (24 hour), a simple extraction of the reaction mixture with aqueous HCl (1 N) separates the catalyst from the product. Evaporation of the organic solvent provides the desired product in high purity (pure by NMR) and excellent yield (95%). The catalyst can be easily recovered quantitatively. Basifying the aqueous phase with KOH followed by extraction of the alkaline aqueous solution with EtOAc and removal of the organic solvent furnished the recovered catalyst in high purity (pure by NMR). The recovered catalyst is used without further treatment for another preparative scale reaction to give a new batch of product without deterioration in ee and yield.

We have demonstrated that the newly uncovered catalytic desymmetrization of meso-cyclic anhydrides mediated by the commercially available aryl ethers of chinchona alkaloids is a general, highly selective and practical catalytic asymmetric transformation. The reaction described here represents the first catalytic reaction that provides straightforward accesses toward both enantiomers of a broad range of valuable chiral hemiesters in high optical purity. It is important to note that most of these chiral hemiesters have been employed in the syntheses of various natural products and biologically important compounds.[1-8] The availability of the catalyst, the simple experimental procedure and the easy yet quantitative recovery of the catalyst renders this reaction a highly attractive synthetic method. Studies aiming to expand the synthetic utility of the reaction and to gain mechanistic insights into the origin of highly selective catalysis are in progress.

References and Notes for Example 1

1. Toyota, M.; Yokota, M.; Ihara, M. *Organic Lett.* 1999, 1, 1627–1629.
2. Couche, E.; Deschatrettes, R.; Poumellec, K.; Bortolussi, M.; Mandvile, G.; Bloch, R. *Synlett.* 1999, 87–88.
3. Paterson, I.; Cowden, C. J.; Woodrow, M. D. *Tetrahedron Lett.* 1998, 39, 6037–6040.
4. a) Borzilleri, R. B.; Weinreb, S. M. *J. Am. Chem. Soc.* 1994, 116, 9789–9790. b) Borzilleri, R. B.; Weinreb, S. M.; Parvez, M. *J. Am. Chem. Soc.* 1995, 117, 10905–10913.
5. Marie, F. B. C.; Mackiewicz, P.; Roul, J. M.; Buendia, J. *Tetrahedron Lett.* 1992, 33, 4889–4892.
6. a) Ohtani, M.; Matsuura, T.; Watanabe, F.; Narisada, M. *J. Org. Chem.* 1991, 56, 4120–4123. b) Ohtani, M.; Matsuura, T.; Watanabe, F.; Narisada, M. *J. Org. Chem.* 1991, 56, 2122–2127.
7. Wender, P. A.; Singh, S. K. *Tetrahedron Lett.* 1990, 31, 2517–1520.
8. Suzuki, T.; Tomino, A.; Matsuda, Y.; Unno, K.; Kametani, T. *Heterocycles,* 1980, 14, 1735–1738.
9. a) Heathcock, C. H.; Hadley, C. R.; Rosen, T.; Theisen, P. D.; Hecker, S. J. *J. Med. Chem.* 1987, 30, 1858–1873. b) Hecker, S. J.; Heathcock, C. H. *J. Am. Chem. Soc.* 1986, 108, 4586–4594. c) Rosen, T.; Heathcock, C. H. *J. Am. Chem. Soc.* 1985, 107, 3731–3733.
10. For representative examples of chiral auxiliary-based methods see: a) Albers, T.; Biagini, S. C. G.; Hibbs, D. E.; Hursthouse, M. B.; Malik, K. M. A.; North, M.; Uriarte, E.; Zagotto, G. *Synthesis* 1996, 393–398. b) Konoike, T.; Araki, Y. *J. Org. Chem.* 1994, 59, 7849–7854. c) Shimizu, M.; Matsukawa, K.; Fujisawa, T. *Bull. Chem. Soc. Jpn.* 1993, 66, 2128–2130. d) Theisen, P. D.; Heathcock, C. H. *J. Org. Chem.* 1993, 58, 142–146.

11. For most successful examples of chiral mediator-based methods see: a) Seebach, D.; Jaeschke, G.; Wang, Y. M. *Angew. Chem. Int. Ed. Engl.* 1995, 34, 2395–2396. b) Jaeschke, G.; Seebach, D. *J. Org. Chem.* 1998, 63, 1190–1197. c) Bolm, C.; Gerlach, A.; Dinter, C. L. *Synlett.* 1999, 195–196.

12. a) Hiratake, J.; Yamamoto, Y.; Oada, J. *J. Chem. Soc. Chem. Commun.* 1985, 1717–1719. b) Hiratake, J.; Inagaki, M.; Yamamoto, Y.; Oada, J. *J. Chem. Soc. Perkin. Trans. I* 1987, 1053–1058.

13. a) Aitken, R. A.; Gopal, J.; Hirst, J. A. *J. Chem. Soc. Chem. Commun.* 1988, 632–634. b) Aitken, R. A.; Gopal, J. *Tetrahedron: Asymmetry* 1990, 1, 517–520.

14. Ozegowski, R.; Kunath, A.; Schick, H. *Tetrahedron: Asymmetry* 1995, 6, 1191–1194.

15. a) Yamamoto, K.; Nishioka, T.; Oada, J. *Tetrahedra Lett.* 1988, 29, 1717–1720. b) Yamamoto, K.; Yamamoto, K.; Nishioka, T.; Oada, J. *Agric. Biol. Chem.* 1988, 52, 307–3092.

16. Pluim, H. Ph.D. Thesis, University of Groningen, Groningen, The Netherlands, 1982.

17. These modified cinchona alkaloids were first reported by Sharpless and coworkers as highly effective ligands for asymmetric dihydroxylations of alkenes. For leading references, see: a) Sharpless, K. B.; Amberg, W.; Bennani, Y, L.; Crispino, G. A.; Hartung, J.; Jeong, K.-S.; Kwong, H.-L.; Morikawa, K.; Wang, Z.-M.; Xu, D.; Zhang, X.-L. *J. Org. Chem.* 1992, 57, 2768. b) Crispino, G. A.; Jeong, K.-S.; Hartmuth, C. K.; Wang, Z.-M.; Xu, D.; Sharpless, K. B. *J. Org. Chem.* 1993, 58, 3785. c) Becker, H.; Sharpless, K. B. *Angew. Chem., Int. Ed. Engl.* 1996, 35, 451–454. d) Sharpless, K. B.; Amberg, W.; Bennani, Y, L.; Crispino, G. A.; Hartung, J.; Jeong, K.-S.; Kwong, H.-L.; Morikawa, K.; Wang, Z.-M.; Xu, D.; Zhang, X.-L. *J. Org. Chem.* 1991, 56, 4585. e) Hartmuth, C. K.; VanNieuwenhze, M. S.; Sharpless, K. B. *Chem. Rev.* 1994, 94, 2483–2547.

Example 2

General Method for Synthesizing Tertiary Amine Catalysts

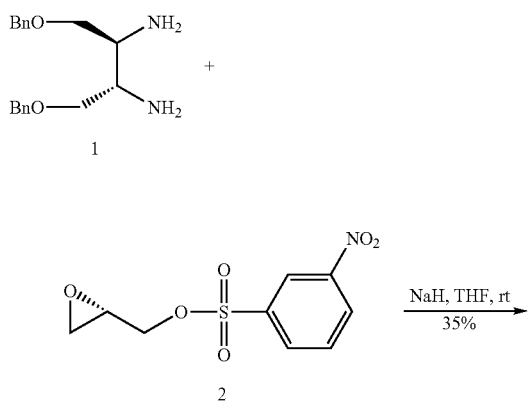

-continued

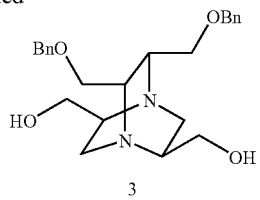

To a solution of diamine 1 (1.40 g, 4.67 mmol) in dry tetrahydrofuran (93 mL) under nitrogen at room temperature was added sodium hydride (60% suspension in mineral oil, 1.87 g, 46.7 mmol). The mixture was stirred for 10 minutes, and then glycidol nosylate 2 was added. After being stirred for 88 hours, the mixture was filtered, and the filtrate was concentrated under reduced pressure. The resulting residue was purified by chromatography [basic aluminum oxide, $CH_3OH:CH_2Cl_2$ (1:100 to 1:20)] to give the chiral tertiary amine 3 (667 mg, 35%) as a white solid.

Example 3

Catalytic Desymmetrization of a Meso Bicyclic Succinic Anhydride Comprising a Urea

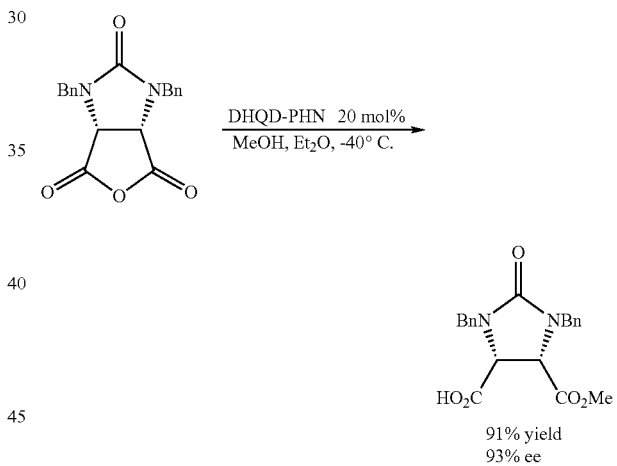

To a mixture of anhydride (16.8 mg, 0.05 mmol) and DHQD-PHN (20 mol %, 5 mg) in $Et_2O$ (2.5 mL) at −40° C., anhydrous MeOH (0.5 mmol, 20.2 ul) cooled at −20° C. was added in one portion. The resulting mixture was stirred until the reaction was complete (~30 hrs) as monitored by TLC (20% MeOH in $CH_2Cl_2$). The reaction was quenched with aqueous HCl (1 N, 3 mL). The aqueous layer was extracted with EtOAc (2×10 mL). The combined organic layer was dried over $MgSO_4$ and concentrated. The residue was purified by flash chromatography (100% $CH_2Cl_2$ to 10% MeOH in $CH_2Cl_2$) to afford the hemiester (16.7 mg, 91% yield). The ee of the hemiester was determined to be 93% by converting the hemiester into the corresponding ester amide (*J. Chem. Soc. Perkin. Trans I* 1987, 1053) via a reaction of the hemiester with (R)-1-(1-napthyl) ethyl amine. The ester amide was analyzed by chiral HPLC (Chiralpak, OD, 280 nm, 0.6 mL/min; retention times for the relevant diastereomers are 20.030 and 25.312 minutes, respectively).

Example 4

Catalytic Desymmetrization of a Meso Bicyclic Succinic Anhydride Comprising a Ketone

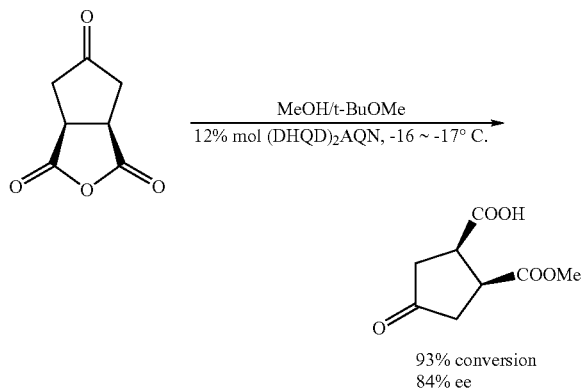

93% conversion
84% ee

Dry methanol (32 mg, 1.0 mmol) was added dropwise to a stirred solution of the anhydride (0.1 mol, 15.4 mg) and (DHQD)$_2$AQN (12% mol, 10.3 mg) in t-butyl methyl ether at −16~−17° C. The reaction mixture was stirred at that temperature for 80 hrs. The reaction was then quenched with HCl (1 N, 3 mL). The aqueous phase was extracted with EtOAc (2×15 mL). The organic phase was combined, dried over Na$_2$SO$_4$, and the solvent was removed under reduced pressure. The ee of the hemiester was determined to be 84% by converting the hemiester into the corresponding ester amide (*J. Chem. Soc. Perkin. Trans I* 1987, 1053) via a reaction of the hemiester with (R)-1-(1-napthyl) ethyl amine. It was analyzed by HPLC (Hypersil SI 4.6×200 mm, 280 nm, 0.5 mL/min, Hexanes: i-Propanol=9:1; retention times for the relevant diastereomers are 28.040 and 33.479 minutes, respectively).

Example 5

General Procedure for the Alcoholysis of 2,3-Dimethyl succinic Anhydride Using QD-PP as Catalyst

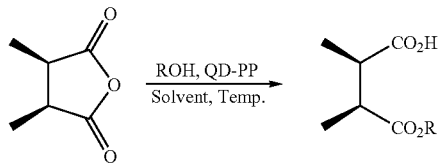

Alcohol (0.1–1.0 mmol) was added to a solution of anhydride (0.1–0.2 mmol) and QD-PP (20–100 mol %) in ether (0.5–5.0 mL) at the reaction temperatures indicated in the Figures. The reaction mixture was initially stirred and then allowed to sit at that temperature until the starting material was consumed as indicated by TLC analysis (43 h) or Chiral GC (β-CD) analysis (0.5–101 h). The reaction was quenched by adding HCl (1 N, 5 mL) in one portion. The aqueous phase was extracted with ether (2×20 mL). The organic phase was combined, dried over Na$_2$SO$_4$, and concentrated to provide the desired product without further purification. The enantiomeric excess (ee) of each product was determined by HPLC analysis of a diastereoisomeric mixture of the corresponding amide-ester prepared from the hemiester according to a modified literature procedure below or chiral GC analysis.

Modified Literature Procedure for Determining the Enantiomeric Excess of Products (J. Hiratake, M. Inagaki, Y Yamamoto, J Oda, J. Chem. Soc., Perkin Trans. 1 1987, 1053.)

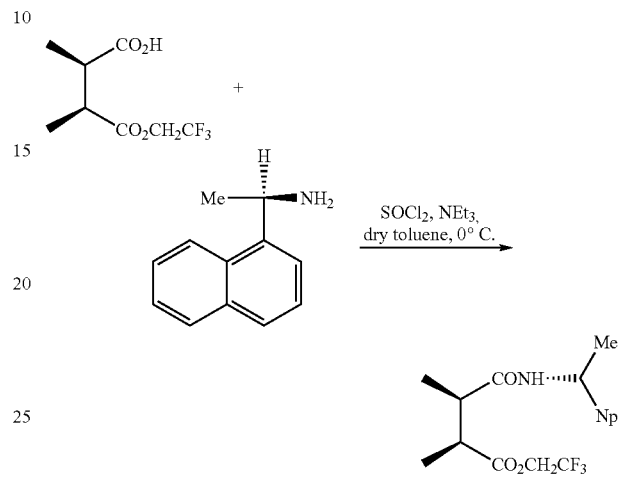

To a solution of hemiester (0.1 mmol) in dry toluene (3 mL) at 0° C. was added thionyl chloride (14.3 mg, 0.12 mmol). The mixture was allowed to stir at 0° C. for 10 min followed by the addition of (R)-1-(1-naphthyl)ethylamine (18.8 mg, 0.11 mmol) and triethylamine (33.4 mg, 0.33 mmol), respectively. The resulting mixture was allowed to stir for 30 minutes at 0° C. followed by another 30 minutes at room temperature. The reaction was then quenched with HCl (1 N, 5 mL), diluted with EtOAc (20 mL), and washed with saturated NaHCO$_3$ (5 mL) and saturated brine (5 mL), respectively. The organic layer was dried with Na$_2$SO$_4$.

Example 6

General Procedure for the Alcoholysis of Meso Substituted Succinic Anhydrides Using QD-PP in Ether

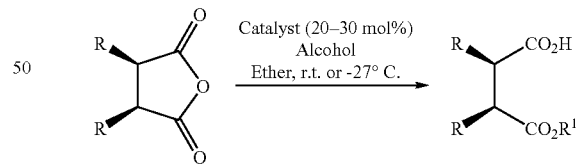

Figure 11:
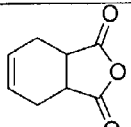
FIG. 11 depicts the results from desymmetrization of a number of meso cyclic anhydrides. In each case: the amount of substrate was 0.1 mmol; the concentration of the substrate was 0.02 M; and the solvent was ether.
Figure 11:
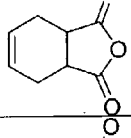
Figure 11:
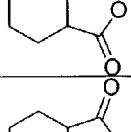
Figure 11:
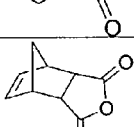
Figure 11:
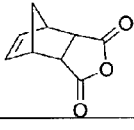
Figure 12:
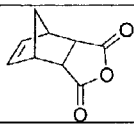
FIG. 12 depicts the results from desymmetrization of a number of meso cyclic anhydrides. In each case: the amount of substrate was 0.1 mmol; the concentration of the substrate was 0.02 M; and the solvent was ether.
Figure 12:
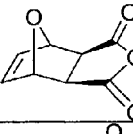
Figure 12:
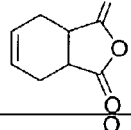
Figure 12:
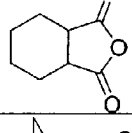
Figure 12:
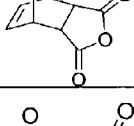
Figure 12:
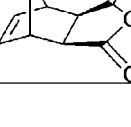

Alcohol (1.0 mmol) was added to a solution of anhydride (0.1 mmol) and QD-PP (20–100 mol %) in ether (5.0 mL) at the reaction temperature indicated in the Figures. See, e.g., FIGS. 11 and 12. The reaction mixture was initially stirred and then allowed to sit at that temperature until the starting material is consumed as indicated by TLC analysis (2–72 h). The reaction was quenched by adding HCl (1 N, 3 mL) in one portion. The aqueous phase was extracted with ether (2×10 mL). The organic phase was combined, dried over Na$_2$SO$_4$, and concentrated to provide the desired product without further purification. The product was determined pure as indicated by NMR). The enantiomeric excess (ee) of each product was determined by HPLC analysis of a diastereoisomeric mixture of the corresponding amide-ester prepared from the hemiester according to the modified literature procedure below.

Modified Literature Procedure for Determining the Enantiomeric Excess of Products (J. Hiratake, M. Inagaki, Y Yamamoto, J. Oda, J. Chem. Soc., Perkin Trans. 1 1987, 1053.)

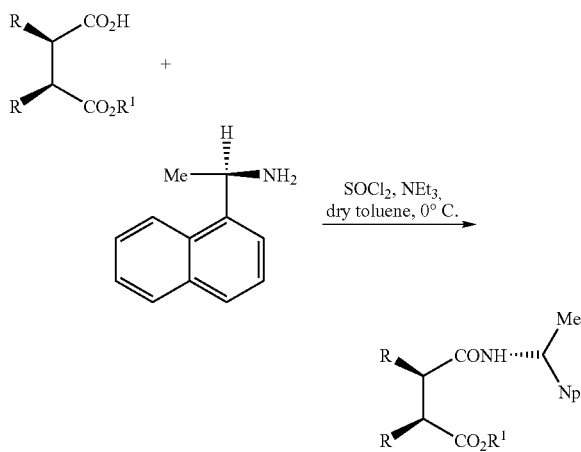

To a solution of hemiester (0.1 mmol) in dry toluene (3 mL) at 0° C. was added thionyl chloride (14.3 mg, 0.12 mmol). The mixture was allowed to stir at 0° C. for 10 min followed by the addition of (R)-1-(1-naphthyl)ethylamine (18.8 mg, 0.11 mmol) and triethylamine (33.4 mg, 0.33 mmol), respectively. The resulting mixture was allowed to stir for 30 minutes at 0° C. followed by another 30 minutes at room temperature. The reaction was then diluted with EtOAc (20 mL) and washed successively with HCl (1 N, 10 mL), saturated $NaHCO_3$ (10 mL) and saturated brine (10 mL). The organic layer was dried with $Na_2SO_4$.

INCORPORATION BY REFERENCE

All of the patents and publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method of preparing a chiral, non-racemic compound from a prochiral substituted cyclic anhydride or a meso substituted cyclic anhydride, comprising the step of:
reacting a prochiral substituted cyclic anhydride or a meso substituted cyclic anhydride with a nucleophile in the presence of a chiral, non-racemic tertiary amine catalyst; wherein said prochiral substituted cyclic anhydride or said meso substituted cyclic anhydride comprises an internal plane of symmetry or point of symmetry or both; wherein said meso substituted cyclic anhydride comprises at least two chiral centers; and wherein said nucleophile is an alcohol, thiol or amine; thereby producing a chiral, non-racemic compound.

2. The method of claim 1, wherein said prochiral substituted cyclic anhydride or meso substituted cyclic anhydride is a substituted succinic anhydride or a substituted glutaric anhydride.

3. The method of claim 1, wherein said nucleophile is an alcohol.

4. The method of claim 1, wherein said nucleophile is a primary alcohol.

5. The method of claim 1, wherein said nucleophile is methanol or $CF_3CH_2OH$.

6. The method of claim 1, wherein said chiral, non-racemic tertiary amine catalyst is Q-PP, Q-TB, QD-PP, QD-TB, $(DHQ)_2PHAL$, $(DHQD)_2PHAL$, $(DHQ)_2PYR$, $(DHQD)_2PYR$, $(DHQ)_2AQN$, $(DHQD)_2AQN$, DHQ-CLB, DHQD-CLB, DHQ-MEQ, DHQD-MEQ, DHQ-AQN, DHQD-AQN, DHQ-PHN, or DHQD-PHN.

7. The method of claim 1, wherein said chiral, non-racemic tertiary amine catalyst is DHQD-PHN or $(DHQD)_2$AQN.

8. The method of claim 1, wherein said chiral, non-racemic tertiary amine catalyst is Q-PP, Q-TB, QD-PP or QD-TB.

9. The method of claim 1, wherein said chiral, non-racemic tertiary amine catalyst is QD-PP.

10. The method of claim 1, wherein said prochiral substituted cyclic anhydride or meso substituted cyclic anhydride is a substituted succinic anhydride or substituted glutaric anhydride; said nucleophile is an alcohol; and said chiral, non-racemic tertiary amine catalyst is Q-PP, Q-TB, QD-PP, QD-TB, $(DHQ)_2PHAL$, $(DHQD)_2PHAL$, $(DHQ)_2PYR$, $(DHQD)_2PYR$, $(DHQ)_2AQN$, $(DHQD)_2AQN$, DHQ-CLB, DHQD-CLB, DHQ-MEQ, DHQD-MEQ, DHQ-AQN, DHQD-AQN, DHQ-PHN, or DHQD-PHN.

11. The method of claim 1, wherein said prochiral substituted cyclic anhydride or meso substituted cyclic anhydride is a substituted succinic anhydride or substituted glutaric anhydride; said nucleophile is a primary alcohol; and said chiral, non-racemic tertiary amine catalyst is Q-PP, Q-TB, QD-PP, QD-TB, $(DHQ)_2PHAL$, $(DHQD)_2PHAL$, $(DHQ)_2PYR$, $(DHQD)_2PYR$, $(DHQ)_2AQN$, $(DHQD)_2AQN$, DHQ-CLB, DHQD-CLB, DHQ-MEQ, DHQD-MEQ, DHQ-AQN, DHQD-AQN, DHQ-PHN, or DHQD-PHN.

12. The method of claim 1, wherein said prochiral substituted cyclic anhydride or meso substituted cyclic anhydride is a substituted succinic anhydride or substituted glutaric anhydride; said nucleophile is methanol or $CF_3CH_2OH$; and said chiral, non-racemic tertiary amine catalyst is Q-PP, Q-TB, QD-PP, QD-TB, $(DHQ)_2PHAL$, $(DHQD)_2PHAL$, $(DHQ)_2PYR$, $(DHQD)_2PYR$, $(DHQ)_2AQN$, $(DHQD)_2AQN$, DHQ-CLB, DHQD-CLB, DHQ-MEQ, DHQD-MEQ, DHQ-AQN, DHQD-AQN, DHQ-PHN, or DHQD-PHN.

13. The method of claim 1, wherein said prochiral substituted cyclic anhydride or meso substituted cyclic anhydride is a substituted succinic anhydride or substituted glutaric anhydride; said nucleophile is an alcohol; and said chiral, non-racemic tertiary amine catalyst is DHQD-PHN or $(DHQD)_2AQN$.

14. The method of claim 1, wherein said prochiral substituted cyclic anhydride or meso substituted cyclic anhydride is a substituted succinic anhydride or substituted glutaric anhydride; said nucleophile is a primary alcohol; and said chiral, non-racemic tertiary amine catalyst is DHQD-PHN or $(DHQD)_2AQN$.

15. The method of claim 1, wherein said prochiral substituted cyclic anhydride or meso substituted cyclic anhydride is a substituted succinic anhydride or substituted glutaric anhydride; said nucleophile is methanol or CF$_3$CH$_2$OH; and said chiral, non-racemic tertiary amine catalyst is DHQD-PHN or (DHQD)$_2$AQN.

16. The method of claim 1, wherein said prochiral substituted cyclic anhydride or meso substituted cyclic anhydride is a substituted succinic anhydride or substituted glutaric anhydride; said nucleophile is an alcohol; and said chiral, non-racemic tertiary amine catalyst is Q-PP, Q-TB, QD-PP or QD-TB.

17. The method of claim 1, wherein said prochiral substituted cyclic anhydride or meso substituted cyclic anhydride is a substituted succinic anhydride or substituted glutaric anhydride; said nucleophile is a primary alcohol; and said chiral, non-racemic tertiary amine catalyst is Q-PP, Q-TB, QD-PP or QD-TB.

18. The method of claim 1, wherein said prochiral substituted cyclic anhydride or meso substituted cyclic anhydride is a substituted succinic anhydride or substituted glutaric anhydride; said nucleophile is methanol or CF$_3$CH$_2$OH; and said chiral, non-racemic tertiary amine catalyst is Q-PP, Q-TB, QD-PP or QD-TB.

19. The method of claim 1, wherein said prochiral substituted cyclic anhydride or meso substituted cyclic anhydride is a substituted succinic anhydride or substituted glutaric anhydride; said nucleophile is an alcohol; and said chiral, non-racemic tertiary amine catalyst is QD-PP.

20. The method of claim 1, wherein said prochiral substituted cyclic anhydride or meso substituted cyclic anhydride is a substituted succinic anhydride or substituted glutaric anhydride; said nucleophile is a primary alcohol; and said chiral, non-racemic tertiary amine catalyst is QD-PP.

21. The method of claim 1, wherein said prochiral substituted cyclic anhydride or meso substituted cyclic anhydride is a substituted succinic anhydride or substituted glutaric anhydride; said nucleophile is methanol or CF$_3$CH$_2$OH; and said chiral, non-racemic tertiary amine catalyst is QD-PP.

22. The method of claim 1, wherein said chiral, non-racemic tertiary amine catalyst is present in less than about 30 mol % relative to said prochiral substituted cyclic anhydride or meso substituted cyclic anhydride.

23. The method of claim 1, wherein said chiral, non-racemic tertiary amine catalyst is present in less than about 20 mol % relative to said prochiral substituted cyclic anhydride or meso substituted cyclic anhydride.

24. The method of claim 1, wherein said chiral, non-racemic tertiary amine catalyst is present in less than about 10 mol % relative to said prochiral substituted cyclic anhydride or meso substituted cyclic anhydride.

25. The method of claim 1, wherein said chiral, non-racemic compound has an enantiomeric excess greater than about 50%.

26. The method of claim 1, wherein said chiral, non-racemic compound has an enantiomeric excess greater than about 70%.

27. The method of claim 1, wherein said chiral, non-racemic compound has an enantiomeric excess greater than about 90%.

28. The method of claim 1, wherein said chiral, non-racemic compound has an enantiomeric excess greater than about 95%.

* * * * *

UNITED STATES PATENT AND TRADEMARK OFFICE
CERTIFICATE OF CORRECTION

PATENT NO. : 7,053,236 B2
APPLICATION NO. : 10/460051
DATED : May 30, 2006
INVENTOR(S) : Li Deng et al.

Page 1 of 1

It is certified that error appears in the above-identified patent and that said Letters Patent is hereby corrected as shown below:

In the Specification

At Column 1, Line numbers 16-18, please replace:
"The invention was made with support provided by the National Institutes of Health (grant number GM-61591); therefore, the government has certain rights in the invention"

With:
--This invention was made with government support under R01 GM061591 awarded by the National Institutes of Health. The government has certain rights in the invention.--

Signed and Sealed this
Thirteenth Day of August, 2019

Andrei Iancu
*Director of the United States Patent and Trademark Office*